US010251619B2

(12) United States Patent
Park et al.

(10) Patent No.: US 10,251,619 B2
(45) Date of Patent: Apr. 9, 2019

(54) METHOD AND APPARATUS FOR SETTING OPERATING CONDITION OF DETECTOR REGISTERED TO IMAGING SYSTEM BASED ON DETECTOR INFORMATION PRE-STORED IN THE DETECTOR

(71) Applicant: SAMSUNG ELECTRONICS CO., LTD., Suwon-si (KR)

(72) Inventors: Jong-seo Park, Yongin-si (KR); Woo-sup Han, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 898 days.

(21) Appl. No.: 14/540,132

(22) Filed: Nov. 13, 2014

(65) Prior Publication Data

US 2015/0157289 A1 Jun. 11, 2015

(30) Foreign Application Priority Data

Dec. 5, 2013 (KR) .................. 10-2013-0150828

(51) Int. Cl.
*A61B 6/00* (2006.01)
*H04N 5/32* (2006.01)
(Continued)

(52) U.S. Cl.
CPC ............ *A61B 6/545* (2013.01); *A61B 6/4494* (2013.01); *A61B 6/548* (2013.01);
(Continued)

(58) Field of Classification Search
CPC ........... A61B 6/00; A61B 6/42; A61B 6/4266; A61B 6/44; A61B 6/4405; A61B 6/4411;
(Continued)

(56) References Cited

U.S. PATENT DOCUMENTS 6,320,934 B1 * 11/2001 Carroll ..................... A61B 6/14
348/E3.02
2002/0056008 A1 * 5/2002 Keane ..................... H04L 61/00
709/245

(Continued)

FOREIGN PATENT DOCUMENTS

| EP | 2385475 A1 | 11/2011 |
|----|------------|---------|
| EP | 2390682 A2 | 11/2011 |
| EP | 2870916 A1 | 5/2015 |

OTHER PUBLICATIONS

Communication dated Jun. 1, 2015, issued by the European Patent Office in counterpart European Patent Application No. 14193032.1.

*Primary Examiner* — Anastasia Midkiff
(74) *Attorney, Agent, or Firm* — Sughrue Mion, PLLC

(57) ABSTRACT

A method of setting operating conditions of a detector in an imaging system includes searching for a detector that is not registered in the imaging system; acquiring detector profile information from the searched detector; registering the detector based on the detector profile information; allocating a predetermined marker to the registered detector to represent activation or non-activation thereof; transmitting control information including the allocated predetermined marker to the detector; receiving detector correction information from the detector; and setting operating conditions of the detector based on the received detector correction information.

32 Claims, 12 Drawing Sheets

(51) Int. Cl.
  *H04W 8/00* (2009.01)
  *H04W 8/02* (2009.01)
  *H05G 1/56* (2006.01)
  *H04N 5/374* (2011.01)
  *H04W 60/04* (2009.01)
  *H04W 60/06* (2009.01)
  *H04W 72/04* (2009.01)
  *H01L 27/146* (2006.01)
  *H01L 27/148* (2006.01)

(52) U.S. Cl.
  CPC .. *H01L 27/14601* (2013.01); *H01L 27/14806* (2013.01); *H04N 5/3741* (2013.01); *H04W 8/005* (2013.01); *H04W 8/02* (2013.01); *H04W 60/04* (2013.01); *H04W 60/06* (2013.01); *H04W 72/0406* (2013.01); *H05G 1/56* (2013.01); *A61B 2562/08* (2013.01); *H04N 5/32* (2013.01)

(58) Field of Classification Search
  CPC ......... A61B 6/4494; A61B 6/54; A61B 6/545; A61B 6/548; A61B 6/586; A61B 2562/00; A61B 2562/04; A61B 2562/08; H01L 27/00; H01L 27/14; H01L 27/144; H01L 27/146; H01L 27/14601; H01L 27/14658; H01L 27/14676; H01L 27/148; H01L 27/14806; H05G 1/00; H05G 1/08; H05G 1/26; H05G 1/30; H05G 1/56; H04L 12/2858; H04L 12/2859; H04L 12/2861; H04L 12/40117; H04L 12/40123; H04L 12/46; H04L 12/4641; H04N 5/369; H04N 5/374; H04N 5/3741; H04N 5/376; H04N 5/38; H04N 5/44; H04W 8/00; H04W 8/005; H04W 8/02; H04W 8/08; H04W 8/085; H04W 8/10; H04W 8/12; H04W 56/00; H04W 56/001; H04W 60/00; H04W 60/005; H04W 60/04; H04W 60/06; H04W 72/00; H04W 72/005; H04W 72/02; H04W 72/04; H04W 72/0406; H04W 74/00; H04W 74/002; H04W 76/00; H04W 76/02; H04W 92/00; H04W 92/16; H04W 92/18; H04W 92/20; H04W 99/00

See application file for complete search history.

(56) References Cited

U.S. PATENT DOCUMENTS

| | | | |
|---|---|---|---|
| 2012/0124660 A1* | 5/2012 | Wang | H04L 12/4641 726/12 |
| 2012/0189098 A1 | 7/2012 | Liu et al. | |
| 2012/0195407 A1* | 8/2012 | Nenoki | A61B 6/4283 378/98.5 |
| 2014/0016749 A1* | 1/2014 | Oda | H04N 5/32 378/62 |
| 2014/0140277 A1* | 5/2014 | Barrett | H04L 41/0806 370/328 |
| 2015/0063542 A1* | 3/2015 | Park | A61B 6/542 378/62 |

* cited by examiner

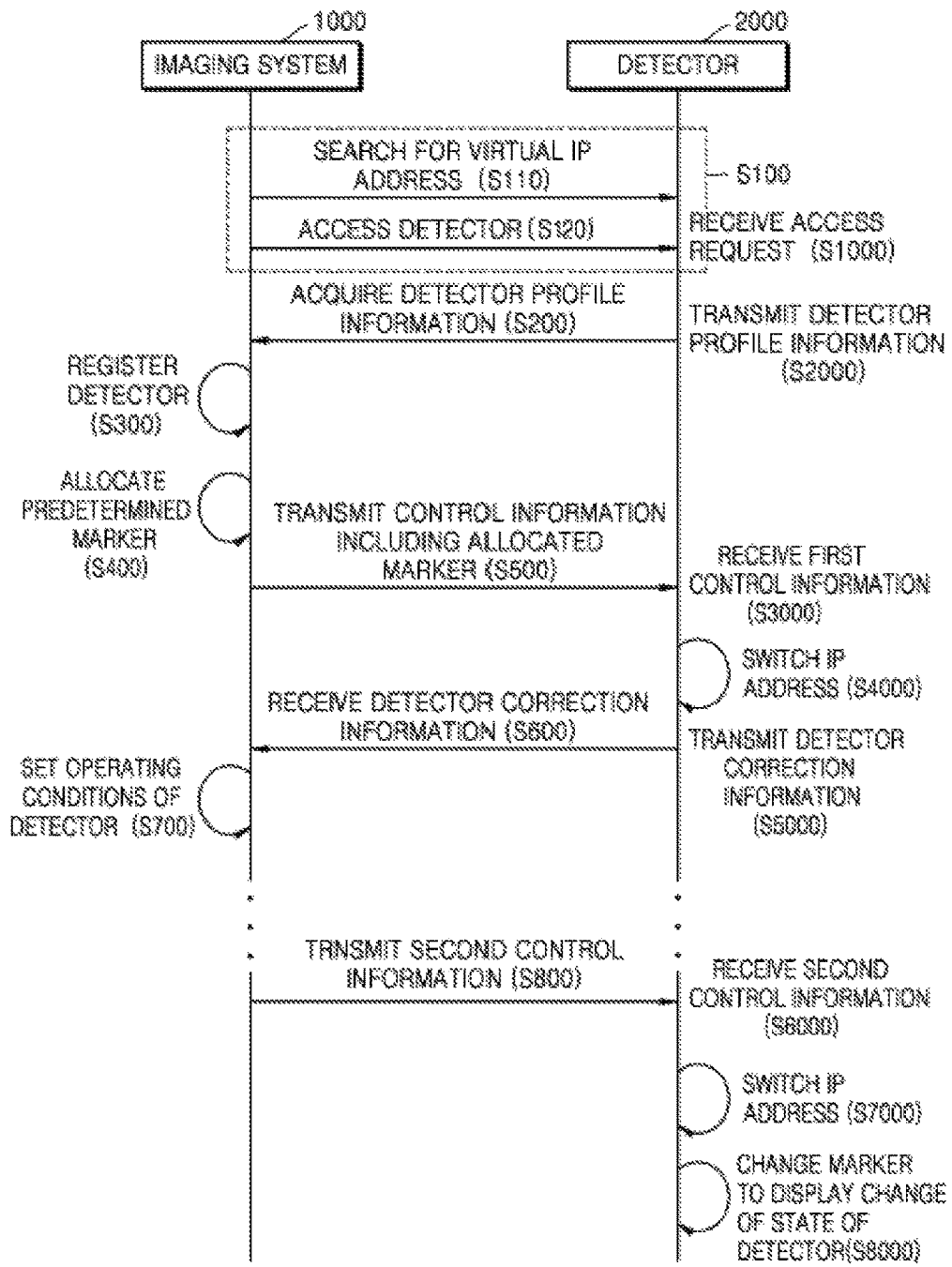

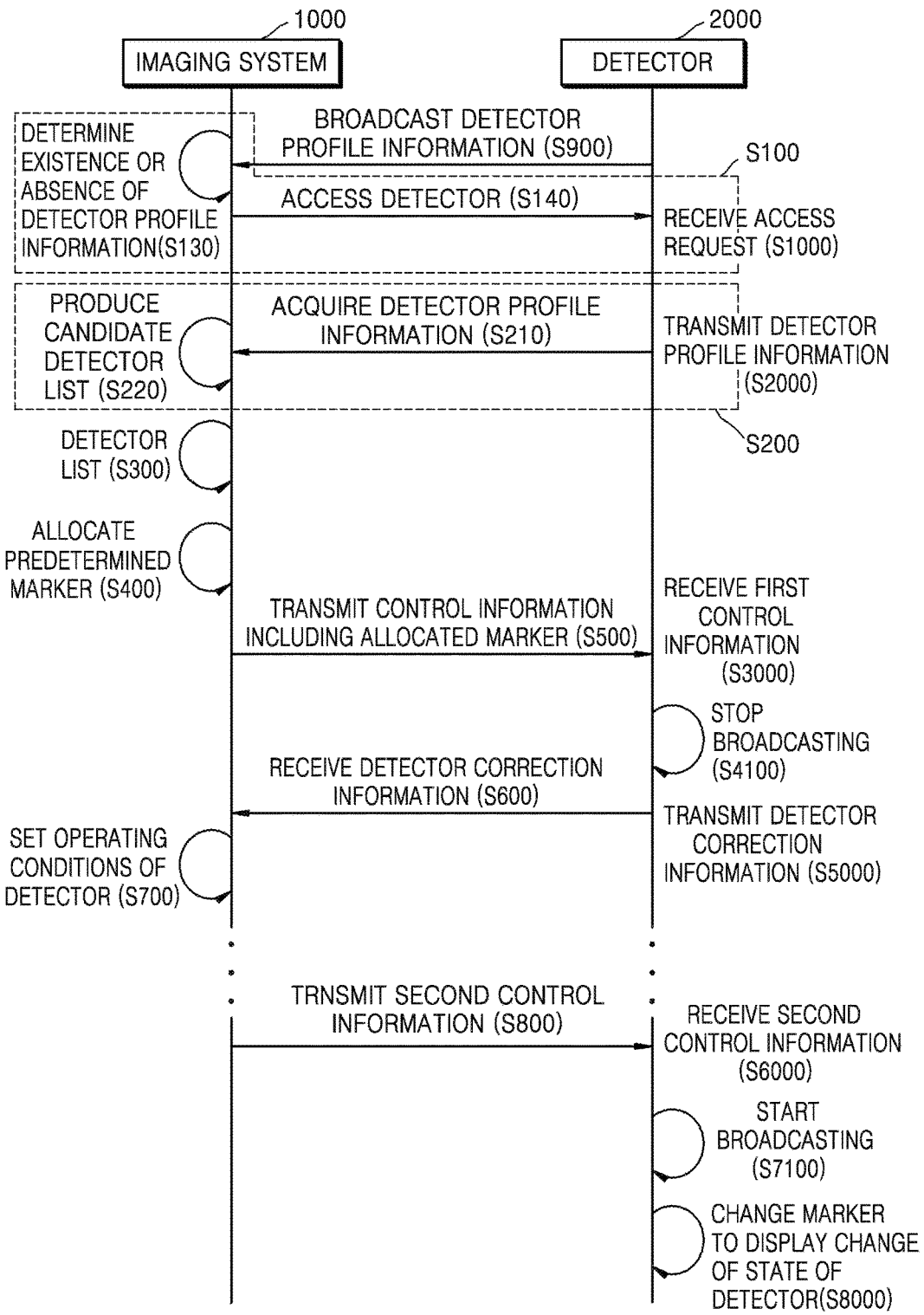

METHOD AND APPARATUS FOR SETTING OPERATING CONDITION OF DETECTOR REGISTERED TO IMAGING SYSTEM BASED ON DETECTOR INFORMATION PRE-STORED IN THE DETECTOR

CROSS-REFERENCE TO RELATED APPLICATION(S)

This application claims priority from Korean Patent Application No. 10-2013-0150828, filed on Dec. 5, 2013, in the Korean Intellectual Property Office, the disclosure of which is incorporated herein in its entirety by reference.

BACKGROUND

1. Field

Apparatuses and methods consistent with exemplary embodiments relate to a method and an apparatus for setting operating conditions of a detector registered in an imaging system, and more particularly, to a method and an apparatus for setting operating conditions of a detector registered in an imaging system based on detector information pre-stored in the detector.

2. Description of the Related Art

In general, X-rays, which are electromagnetic waves having a wavelength of about 0.01 to about 100 Å, can pass through an object. Thus, the X-rays may be commonly used in a wide range of applications, such as medical equipment that captures images of the inside of a living body and non-destructive testing equipment for industrial use.

X-ray imaging apparatuses using X-rays allow X-rays emitted by an X-ray tube (or X-ray source) to pass through an object, and detect a difference between intensities of the passed X-rays by using an X-ray detector to identify an internal structure of the object. X-ray imaging apparatuses may easily identify the internal structure of an object by using a principle that a transmission coefficient of X-rays varies depending on a density of the object and an atomic number of an atom included in the object. As the wavelength of an X-ray becomes shorter, the transmission coefficient of X-rays increases, and a picture on a screen becomes clearer.

An X-ray imaging apparatus generally includes an X-ray source, an X-ray detector, and an image processor. The X-ray source irradiates an X-ray to a target under predetermined X-ray irradiation conditions, and the X-ray detector acquires image data based on an X-ray passed through the object and transmits the image data to the image processor. The image processor may process the image data to provide an image of the object to a display included in the X-ray imaging apparatus.

In other words, when the X-ray emitted from the X-ray source passes through the object, a scintillator included in the X-ray imaging apparatus may change the passed X-ray to visible light depending on a density of the object, and a photodiode included in the X-ray imaging apparatus may change the visible light to an electrical signal. The X-ray imaging apparatus may express a digital image of the object through which the X-ray passes, by using the electrical signal.

SUMMARY

Exemplary embodiments address at least the above problems and/or disadvantages and other disadvantages not described above. Also, exemplary embodiments are not required to overcome the disadvantages described above, and an exemplary embodiment may not overcome any of the problems described above.

One or more exemplary embodiments include a method and an apparatus for setting operation conditions of a detector registered in an imaging system based on detector information pre-stored in the detector.

According to an aspect of an exemplary embodiment, provided is a method of setting operating conditions of a detector in an imaging system including: searching for a detector that is not registered in the imaging system; acquiring detector profile information from the searched detector; registering the detector based on the detector profile information; allocating a predetermined marker to the registered detector to represent activation or non-activation thereof; transmitting control information including the allocated predetermined marker to the detector; receiving detector correction information from the detector; and setting operating conditions of the detector based on the received detector correction information.

The searching may include searching for a virtual Internet Protocol (IP) address of the detector that is not registered in the imaging system; and accessing the detector by using the searched virtual IP address.

The detector profile information may include at least one from among a real IP address, a type, and a serial number of the detector. The registering may include storing the detector profile information to an available detector list of the imaging system.

The predetermined marker may include at least one from among a character, a number, a symbol, a color, and an image.

The receiving may include receiving the detector correction information from the detector via an access to an activated real IP address of the detector. The setting may include setting imaging conditions for performing imaging using the detector based on the detector correction information. The detector correction information may include at least one from among detector step difference correction information indicating an amount of step difference correction of the detector for performing imaging and defective pixel compensation information indicating a range of defective pixel compensation of the detector for performing imaging.

The searching may include determining whether detector profile information is broadcast on a network to which the imaging system is connected; and accessing an unregistered detector corresponding to the detector profile information that is being broadcast on the network.

The acquiring may include receiving the broadcast detector profile information from the unregistered detector; and storing the detector profile information in a candidate detector list.

The detector profile information may include at least one from among a real IP address, a type, and a serial number of the unregistered detector.

The registering may include storing the detector profile information on the candidate detector list to an available detector list of the imaging system.

The receiving may include receiving detector correction information from the detector having the detector profile information stored in the available detector list.

The setting may include setting imaging conditions for performing imaging using the detector, based on the detector correction information received from the detector.

The detector correction information may include at least one from among detector step difference correction information indicating an amount of step difference correction of the detector for performing imaging and defective pixel compensation information indicating a range of defective pixel compensation of the detector for performing imaging.

According an aspect of another exemplary embodiment, provided is a method of transmitting detector correction information of a detector to an imaging system including: receiving, from the imaging system, a request to access the detector via a virtual IP address of the detector; transmitting detector profile information of the detector to the imaging system in response to the request; receiving, from the imaging system, first control information including an allocated predetermined marker; switching the virtual IP address of the detector based on the first control information; and transmitting the detector correction information to the imaging system.

The switching may include deactivating the virtual IP address of the detector and activating the real IP address of the detector; and displaying a change of a state of the detector by using the allocated predetermined marker.

The method may further include receiving second control information from the imaging system; deactivating the real IP address of the detector and activating the virtual IP address of the detector based on the second control information; and displaying a change of the state of the detector by using the allocated predetermined marker.

According to an aspect of an exemplary embodiment, provided is a method of transmitting detector correction information of a detector to an imaging system, the method including: broadcasting detector profile information to a network to which the imaging system is connected; receiving, from the imaging system, first control information including an allocated predetermined marker; and stopping the broadcasting and transmitting, from the detector, the detector correction information to the imaging system based on the first control information.

The stopping may include displaying a change of a state of the detector by using the allocated predetermined marker.

The method may further include receiving second control information from the imaging system; starting broadcasting of the detector profile information to the network based on the second control information; and displaying a change of the state of the detector by using the allocated predetermined marker.

According to an aspect of an exemplary embodiment, provided is an imaging system for setting operating conditions of a detector, the imaging system including: a searcher configured to search for a detector that is not registered in the imaging system; a detector information acquirer configured to acquire detector profile information about the searched detector; a registrator configured to register the detector based on the detector profile information; an allocator configured to allocate a predetermined marker to the detector to represent activation or non-activation thereof; a transmitter configured to transmit control information including the allocated predetermined marker to the detector; a receiver configured to receive detector correction information from the detector; and a setter configured to set operating conditions of the detector based on the received detector correction information.

The searcher may search for a virtual IP address of the detector that is not registered in the imaging system and may access the detector by using the searched virtual IP address.

The registrator may store the detector profile information to an available detector list of the imaging system.

The receiver may receive the detector correction information from the detector by accessing an activated real IP address of the detector. The setter may set imaging conditions for performing imaging using the detector based on the detector correction information. The detector correction information may include at least one from among detector step difference correction information indicating an amount of step difference correction of the detector for performing imaging and defective pixel compensation information indicating a range of defective pixel compensation of the detector for performing imaging.

The searcher may further include a determinator configured to determine whether detector profile information is broadcast on a network to which the imaging system is connected. The searcher may access an unregistered detector corresponding to the detector profile information being broadcast on the network.

The profile information acquirer may receive the broadcast detector profile information from the unregistered detector and store the detector profile information in a candidate detector list.

The detector profile information may include at least one from among a real IP address, a type, and a serial number of the unregistered detector.

The registrator may store the detector profile information on the candidate detector list to an available detector list of the imaging system.

The receiver may receive detector correction information from the detector having the detector profile information stored in the available detector list. The setter may set imaging conditions for performing imaging using the detector based on the detector correction information received from the detector. The detector correction information may include at least one from among detector step difference correction information indicating an amount of step difference correction of the detector for performing imaging and defective pixel compensation information indicating a range of defective pixel compensation of the detector for performing imaging.

According to an aspect of an exemplary embodiment, provided is a detector for transmitting detector correction information to an imaging system, the detector including: a receiver configured to receive a request to access the detector via a virtual IP address of the detector; a transmitter configured to transmit detector profile information of the detector to the imaging system in response to the request, wherein the imaging system registers the detector based on the detector profile information and transmits first control information including an allocated predetermined marker to the detector; a switch configured to switch the virtual IP address of the detector based on the first control information; and the transmitter configured to transmit the detector correction information to the imaging system.

The detector profile information may include at least one from among a real IP address, a type, and a serial number of the detector. The predetermined marker may include at least one from among a character, a number, a symbol, a color, and an image. The detector correction information may include at least one from among detector step difference correction information indicating an amount of step difference correction of the detector for performing imaging and defective pixel compensation information indicating a range of defective pixel compensation of the detector for performing imaging.

The switch may deactivate the virtual IP address of the detector and activate the real IP address of the detector based on the first control information. The detector may further include a display configured to display a change of a state of the detector by using the allocated predetermined marker.

The receiver may receive second control information from the imaging system. The switch may deactivate the real IP address of the detector and activate the virtual IP address of the detector based on the second control information. The display may display a change of the state of the detector by changing the allocated predetermined marker.

According to an aspect of an exemplary embodiment, provided is a detector for transmitting detector correction information to an imaging system, the detector including a broadcaster configured to broadcast detector profile information to a network to which the imaging system is connected; a receiver configured to receive, from the imaging system first control information including an allocated predetermined marker; a controller configured to stop the broadcasting by the detector based on the first control information; and a transmitter configured to transmit the detector correction information to the imaging system.

The detector may further include a display configured to display a change of a state of the detector by using the allocated predetermined marker when the broadcasting by the detector is stopped by the controller.

The receiver may receive second control information from the imaging system. The broadcaster may start broadcasting of detector profile information to the network based on the second control information. The display may display a change of the state of the detector by changing the allocated predetermined marker when the broadcasting by the detector is started.

According to an aspect of an exemplary embodiment, provided is a non-transitory computer-readable recording medium having recorded thereon a program for executing the above described methods.

BRIEF DESCRIPTION OF THE DRAWINGS

The above and/or other aspects will become more apparent by describing certain exemplary embodiments, taken in conjunction with the accompanying drawings in which:

FIG. 6 is a flowchart of a method in which an imaging system and a detector set operating conditions of the detector based on detector information according to an exemplary embodiment;

FIG. 8 is a flowchart of a method in which an imaging system and a detector set operating conditions of the detector based on detector information according to another exemplary embodiment;

DETAILED DESCRIPTION

Figure 1:
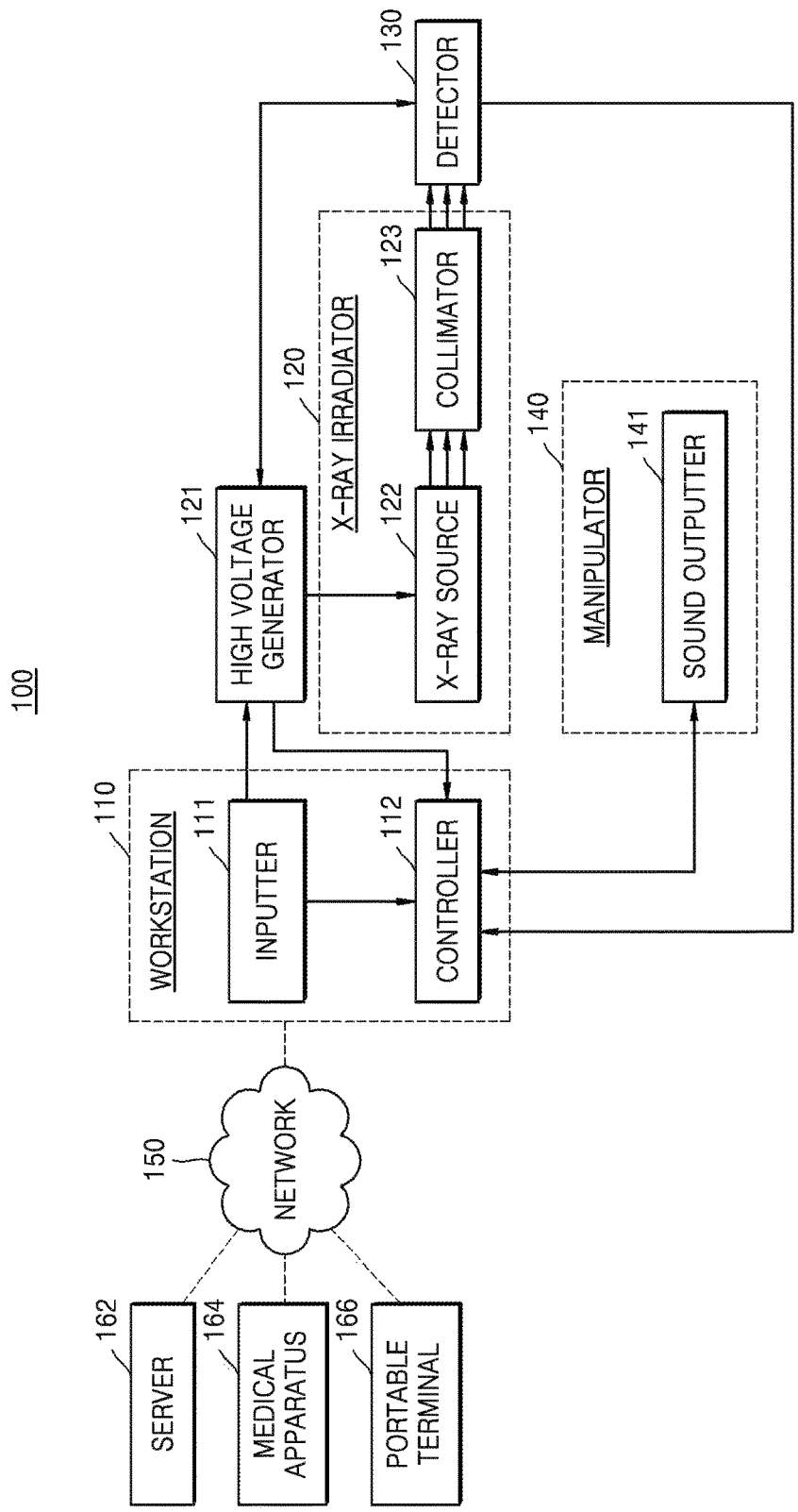
FIG. 1 is a block diagram of an X-ray apparatus according to an exemplary embodiment.

Certain exemplary embodiment will now be described in greater detail with reference to the accompanying drawings. The matters defined in the specification, such as detailed construction and elements, are provided to assist in a comprehensive understanding of the exemplary embodiment. However, the exemplary embodiments may be embodied in many different forms and should not be construed as being limited to the exemplary embodiments set forth herein; rather, these exemplary embodiments are provided such that this disclosure will be thorough and complete, and will fully convey the concept of the exemplary embodiments to one of ordinary skill in the art. Also, well known functions or constructions are not described in detail since they would obscure the exemplary embodiments with unnecessary detail.

Hereinafter, the terms used in the specification will be briefly described, and exemplary embodiments will be described in detail.

The terms used in this specification are those general terms currently widely used in the art in consideration of functions in regard to exemplary embodiments, but the terms may vary according to the intention of one of ordinary skill in the art, precedents, or new technology in the art. Also, specified terms may be selected by the applicant, and in this case, the detailed meaning thereof will be described in the detailed description of exemplary embodiments. Thus, the terms used in the specification should be understood not as simple names but based on the meaning of the terms and the overall description of exemplary embodiments. Expressions such as "at least one of," when preceding a list of elements, modify the entire list of elements and do not modify the individual elements of the list.

In the present specification, the term "image" may denote multi-dimensional data configured by discrete image elements (for example, pixels in a two-dimensional image and voxels in a three-dimensional image). For example, an image may include medical images of an object acquired by an X-ray, a computed tomography (CT), a magnetic resonance imaging (MRI), an ultrasound wave, and other medical image systems.

Also, in the present specification, an object may include a human being or an animal, or a part of the human being or the animal. For example, the object may include organs, such as the liver, the heart, the uterus, the brain, breasts, the abdomen, or blood vessels. Also, the term "object" may include a phantom. The phantom denotes a material having a volume, a density, and an effective atomic number that is nearly equivalent to those of a living organism, and a phantom according to exemplary embodiments may be a spherical phantom having similar properties to those of the human body.

In the present specification, the term "user" may include a medical expert, for example, a doctor, a nurse, a medical specialist, and a medical imaging expert, or an engineer managing medical apparatuses; however, exemplary embodiments are not limited thereto.

An X-ray apparatus is a medical imaging apparatus that acquires images of internal structures of the human body by transmitting an X-ray through the human body. The X-ray apparatus may acquire medical images of a target object more simply within a shorter time than other medical imaging apparatuses including an MRI apparatus and a CT apparatus. Therefore, the X-ray system is widely used in a simple chest photographing, abdomen photographing, skeleton photographing, nasal sinuses photographing, neck soft tissue photographing, and breast photographing.

FIG. 1 is a block diagram of an X-ray apparatus 100 according to an exemplary embodiment. The X-ray apparatus 100 shown in FIG. 1 may be a fixed-type X-ray apparatus or a moveable X-ray apparatus.

Referring to FIG. 1, the X-ray apparatus 100 includes a workstation 110, an X-ray irradiator 120, a high voltage generator 121, and a detector 130.

The workstation 110 includes an inputter 111 through which a user may input commands for manipulating the X-ray apparatus 100 including an X-ray irradiation, and a controller 112 which controls overall operations of the X-ray apparatus 100.

The high voltage generator 121 generates a high voltage for generating X-rays, and applies the high voltage to an X-ray source 122.

The X-ray irradiator 120 includes the X-ray source 122 which receives the high voltage applied from the high voltage generator 121 to generate and irradiate the X-ray, and a collimator 123 for guiding a path of the X-ray irradiated from the X-ray source 122.

The detector 130 detects the X-ray that is irradiated from the X-ray irradiator 120 and transmitted through the object.

Also, the X-ray apparatus 100 may further include a manipulator 140 including a sound outputter 141 which outputs sound representing information relating to a photographing operation such as the X-ray irradiation under a control of the controller 112.

The workstation 110, the X-ray irradiator 120, the high voltage generator 121, and the detector 130 may be connected to each other via wires or wirelessly. When they are connected to each other wirelessly, a device (not shown) for synchronizing clocks with each other may be further included.

The inputter 111 may include a keyboard, a mouse, a touch screen, a voice recognizer, a fingerprint recognizer, an iris recognizer, and the like. The user may input a command for irradiating the X-ray via the inputter 111. For example, the inputter 111 may include a switch for inputting the command. The switch may be configured such that the switch needs to be separately manipulated to input an irradiation command for irradiating the X-ray. For example, the irradiation command for irradiating the X-ray may be input only when the switch is pushed twice.

That is, in an exemplary embodiment, when the user pushes the switch, a prepare command for performing a pre-heating operation for X-ray irradiation may be input through the switch, and when the user pushes the switch once more, the irradiation command for irradiating the X-ray may be substantially input through the switch. When the user manipulates the switch as described above, the inputter 111 generates signals corresponding to the commands input through the switch manipulation, e.g., a prepare signal and an irradiation signal, and outputs the generated signals to the high voltage generator 121 generating a high voltage for generating the X-ray.

When the high voltage generator 121 receives the prepare signal output from the inputter 111, the high voltage generator 121 starts a pre-heating operation, and when the pre-heating is finished, the high voltage generator 121 outputs a ready signal to the controller 121. In addition, the detector 130 also needs to prepare for detecting the X-ray, and thus, when the high voltage generator 121 receives the prepare signal output from the inputter 111, the high voltage generator 121 outputs the prepare signal to the detector 130 while performing the pre-heating operation, so that the detector 130 may prepare for detecting the X-ray transmitted through the object. The detector 130 prepares for detecting the X-ray in response to the prepare signal, and when the preparing for the detection is finished, the detector 130 outputs a ready signal to the high voltage generator 121 and the controller 112.

When the pre-heating operation of the high voltage generator 121 is finished, the detector 130 is ready for the detecting the X-ray, and the irradiation signal is output from the inputter 111 to the high voltage generator 121, the high voltage generator 121 generates and applies the high voltage to the X-ray source 122, and the X-ray source 122 irradiates the X-ray.

When the irradiation signal is output from the inputter 111, the controller 112 may output a sound output signal to the sound outputter 141 so that the sound outputter 141 outputs predetermined sound and the object may recognize the irradiation of X-ray. Also, the sound outputter 141 may output sound representing other information relating to the photographing, in addition to the X-ray irradiation. In FIG. 1, the sound outputter 141 is included in the manipulator 140; however, exemplary embodiments are not limited thereto, and the sound outputter 141 may be located at a different location from the manipulator 140. For example, the sound outputter 141 may be included in the workstation 110, or may be located on a wall surface of an examination room in which the X-ray photographing of the object is performed.

The controller 112 controls locations of the X-ray irradiator 120 and the detector 130, a photographing timing, and photographing conditions according to photographing conditions set by the user.

In more detail, the controller 112 controls the high voltage generator 121 and the detector 130 according to the command input via the inputter 111 to control an irradiation timing of the X-ray, an intensity of the X-ray, and an irradiation region of the X-ray. Also, the controller 112 adjusts the location of the detector 130 according to a predetermined photographing condition, and controls an operation timing of the detector 130.

In addition, the controller 112 generates a medical image of the object by using image data transmitted from the detector 130. In particular, the controller 121 receives the image data from the detector 130, and generates the medical image of the object by removing noise in the image data, and adjusting a dynamic range and interleaving of the image data. The controller 112 may include one or more hardware and/or software components. For example, the controller 112 may include one or more of an integrated circuitry, a dedicated circuit, firmware, and/or a processor such as a central processing unit (CPU) which executes software programs stored in a storage, e.g., a memory.

The X-ray apparatus 100 shown in FIG. 1 may further include an outputter (not shown) for outputting the medical image generated by the controller 112. The outputter may output information for allowing the user to manipulate the X-ray apparatus 100, for example, a user interface (UI), user information, or object information. The outputter may include, for example, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and other various output devices.

The workstation 110 shown in FIG. 1 may further include a communicator (not shown) that may be connected to a server 162, a medical apparatus 164, and a portable terminal 166 via a network 150.

The communicator may be connected to the network 150 via wires or wirelessly to communicate with the external server 162, the external medical apparatus 164, or the external portable terminal 166. The communicator may transmit or receive data relating to diagnosis of the object via the network 150, and may transmit or receive medical images captured by the external medical apparatus 164, for example, a CT, an MRI, or an X-ray apparatus. Moreover, the communicator may receive a medical history or a treatment schedule of an object (e.g., a patient) from the server 162 to diagnose a disease of the object. Also, the communicator may perform data communication with the portable terminal 166 such as a mobile phone, a personal digital assistant (PDA), or a laptop computer of, for example, a doctor or a patient, as well as the server 162 or the medical apparatus 164 in a hospital.

The communicator may include one or more elements for communicating with external apparatuses, for example, a short distance communication module, a wired communication module, and a wireless communication module.

The short distance communication module may include a module for communicating with a device located within a predetermined distance. The short distance communication module may use short distance communication technology including, for example, wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, exemplary embodiments are not limited thereto.

The wired communication module may include a module for communicating by using an electric signal or an optical signal, and the wired communication module may use wired communication technology including, for example, wired communication technology using a pair cable, a coaxial cable, or an optical fiber cable, or the like; however, exemplary embodiments are not limited thereto.

The wireless communication module may transmit and/or receive a wireless signal to/from at least one of a base station, an external device, and a server in a mobile communication network. Here, the wireless signal may be a voice call signal, a video call signal, or various types of data according to transmission of text and/or multimedia messages.

The X-ray apparatus 100 shown in FIG. 1 may include a plurality of digital signal processors (DSPs) (not shown), an ultra-small calculator (not shown), and a processing circuit (not shown) for specialized usage (for example, a high speed analog/digital (A/D) conversion, a high speed Fourier transformation, an array process, etc.).

In addition, the communication between the workstation 110 and the X-ray generator 120, the workstation 110 and the high voltage generator 211, and the workstation 110 and the detector 130 may use a high speed digital interface including, for example, low voltage differential signaling (LVDS), asynchronous serial communication such as universal asynchronous receiver transmitter (UART), synchronous serial communication, or a low latency network protocol such as a controller area network (CAN), and other various communication methods.

Figure 2:
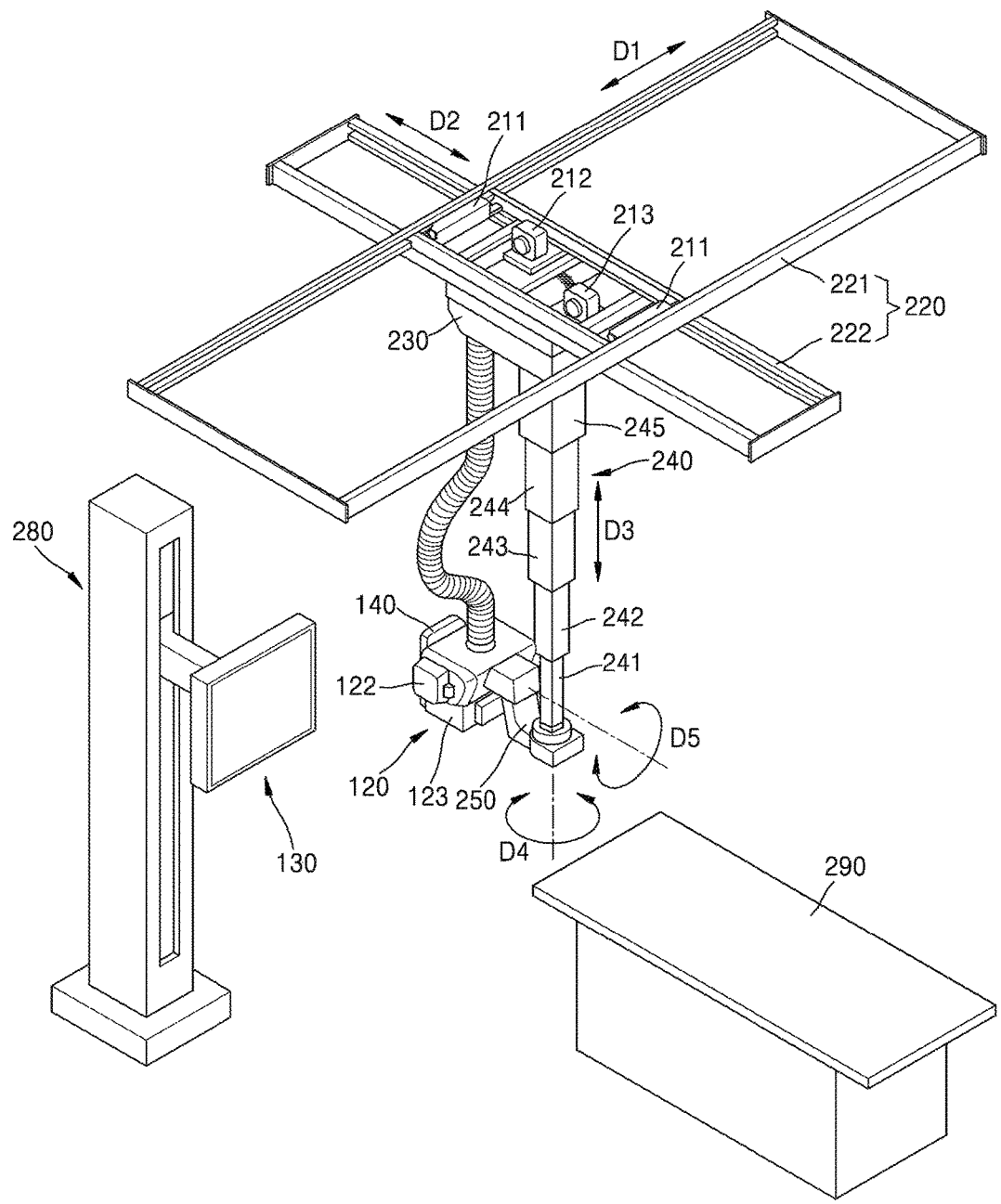
FIG. 2 is a perspective view of a fixed type X-ray apparatus according to an exemplary embodiment.

FIG. 2 is a perspective view of a fixed type X-ray apparatus 200 according to an exemplary embodiment.

As shown in FIG. 2, the X-ray apparatus 200 includes a manipulator 140 for providing a user with an interface for manipulating the X-ray apparatus 200, an X-ray irradiator 120 for irradiating the X-ray to an object, a detector 130 for detecting the X-ray passing through the object, first through third motors 211, 212, and 213 for providing a driving power to transport the X-ray irradiator 120, a guide rail 220, a moving carriage 230, and a post frame 240 to transport the X-ray irradiator 120 by using the driving power of the motors 211, 212, and 213.

The guide rail 220 includes a first guide rail 221 and a second guide rail 222 arranged to have a predetermined angle with respect to each other. The first guide rail 221 and the second guide rail 222 may respectively extend in directions to substantially cross each other.

The first guide rail 221 may be provided on a ceiling of the examination room in which the X-ray apparatus 200 is disposed.

The second guide rail 222 may be located under the first guide rail 221, and may be mounted to the first guide rail 221 to slide along the first guide rail 221. A roller (not shown) that may move along the first guide rail 221 may be provided on the first guide rail 221. The second guide rail 222 is connected to the roller (not shown) to move along the first guide rail 221.

A first direction D1 is defined as a direction in which the first guide rail 221 is extended, and a second direction D2 is defined as a direction in which the second guide rail 222 is extended. The first direction D1 and the second direction D2 may substantially cross each other, and may be substantially parallel to the ceiling of the examination room.

The moving carriage 230 may be disposed under the second guide rail 222 to move along the second guide rail 222. A roller (not shown) moving along the second guide rail 222 may be provided on the moving carriage 230.

Therefore, the moving carriage 230 may move in the first direction D1 together with the second guide rail 222 along the first guide rail 221, and may move in the second direction D2 along the second guide rail 222.

The post frame 240 may be fixed on the moving carriage 230 and located under the moving carriage 230. The post frame 240 may include a plurality of posts 241, 242, 243, 244, and 245.

The plurality of posts 241, 242, 243, 244, and 245 are connected to each other while being insertable into each other. Thus, the post frame 240 may have a length that is adjustable in an up and down direction from the moving carriage 230.

A third direction D3 is defined as a direction in which the length of the post frame 240 is increased or reduced. Therefore, the third direction D3 may substantially cross the first direction D1 and the second direction D2.

The X-ray irradiator 120 may include an X-ray source 122 for generating the X-ray, and a collimator 123 for adjusting an irradiation region of the X-ray that is generated and irradiated from the X-ray source 122. The X-ray source 122 includes an X-ray tube that may be realized as a diode including a cathode and an anode. An inside of the X-ray tube is set as a higher vacuum state of about 10 mmHg, and a filament of the anode is heated to a higher temperature to generate thermal electrons. The filament may be a tungsten filament, and a voltage of about 10 V and a current of about 3 to 5 A may be applied to an electric wire connected to the filament to heat the filament.

In addition, when a higher voltage of about 10 to about 300 kvp is applied between the cathode and the anode, the thermal electrons are accelerated to crash onto a target material of the cathode such that an X-ray is generated. The X-ray is irradiated to outside via a window, and the window may be provided as a beryllium thin film. Here, a portion of the energy of the electrons colliding with the target material is consumed as heat, and a remaining portion of the energy is converted into the X-ray.

The cathode may mainly comprise copper, and the target material may be disposed at an opposite side to the anode. The target material may be a higher resistive material such as, for example, Cr, Fe, Co, Ni, W, or Mo. The target material may be rotated by a rotating field. When the target material is rotated, an electron impact area is increased, and a heat accumulation rate per unit area may be increased about ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value thereof (kvp). When the tube voltage increases, a velocity of the thermal electrons increases, and accordingly, an energy of the X-ray (energy of a photon) that is generated when the thermal electrons collide with the target material is increased. A current flowing in the X-ray tube is referred to as a tube current that may be expressed as an average value thereof (mA). When the tube current increases, the number of thermal electrons emitted from the filament is increased, and accordingly, a dose of the X-ray (the number of X-ray photons) generated when the thermal electrons collide with the target material is increased.

Therefore, the energy of the X-ray may be adjusted according to the tube voltage, and the intensity or dose of the X-ray may be adjusted according to the tube current and a X-ray exposure time.

The high voltage generator 121 may be within the X-ray source 122; however, exemplary embodiments are not limited thereto. For example, the high voltage generator 121 may be at another portion of the X-ray apparatus 200.

The detector 130 may be a digital detector for detecting the X-ray passing through the object, and may be realized as a table type having a table 290 or a stand type having a stand 280. The detector 130 may be provided by using a thin film transistor (TFT) or a charge coupled device (CCD).

A rotating joint 250 may be disposed between the X-ray irradiator 120 and the post frame 240. The rotating joint 250 allows the X-ray irradiator 120 to be coupled to the post frame 240, and supports a load applied to the X-ray irradiator 120.

The X-ray irradiator 120 connected to the rotating joint 250 may rotate on a plane that is substantially perpendicular to the third direction D3. Here, a rotating direction of the X-ray irradiator 120 may be defined as a fourth direction D4.

Also, the X-ray irradiator 120 may be configured to be rotatable on a plane substantially perpendicular to the ceiling of the examination room. Here, a rotating direction of the X-ray irradiator 120 may be defined as a fifth direction D5. Therefore, the X-ray irradiator 120 may rotate in the fourth direction D4 or the fifth direction D5 based on an axis that is substantially parallel with the first direction D1 or the second direction D2, with respect to the rotating joint 250.

The motors 211, 212, and 213 may be provided to move the X-ray irradiator 120 in the first through third directions D1, D2, and D3. The motors 211, 212, and 213 may be electrically driven, and the motors 211, 212, and 213 may respectively include an encoder.

The motors 211, 212, and 213 may be disposed on various locations in consideration of design convenience. For example, the first motor 211 for moving the second guide rail 222 in the first direction D1 may be disposed around the first guide rail 221, the second motor 212 for moving the moving carriage 230 in the second direction D2 may be disposed around the second guide rail 222, and the third motor 213 for increasing or reducing the length of the post frame 240 in the third direction D3 may be disposed in the moving carriage 230. In another example, the first through third motors 211, 212, and 213 may be connected to a driving power transfer unit (not shown) to substantially linearly move the X-ray irradiator 120 in the first through third directions D1, D2, and D3, respectively. The driving power transfer unit may be, for example, a belt and a pulley, a chain and a sprocket, or a shaft.

As another example, the motors 211, 212, and 213 may be disposed between the rotating joint 250 and the post frame 240 and between the rotating joint 250 and the X-ray irradiator 120 to rotate the X-ray irradiator 120 in at least one of the fourth direction D4 and the fifth direction D5.

The manipulator 140 for providing the user with the interface for inputting various information about X-ray photographing and manipulating the X-ray apparatus 200 may be disposed at, for example, a side surface of the X-ray irradiator 120.

Although FIG. 2 shows the fixed type X-ray apparatus 200 connected to the ceiling of the examination room, the X-ray apparatus 200 of FIG. 2 is merely given as an example for convenience of comprehension. That is, the X-ray apparatus according to exemplary embodiments may be an X-ray apparatus having various structures including, for example, a C-arm-type X-ray apparatus and an angiography X-ray apparatus.

Figure 3:
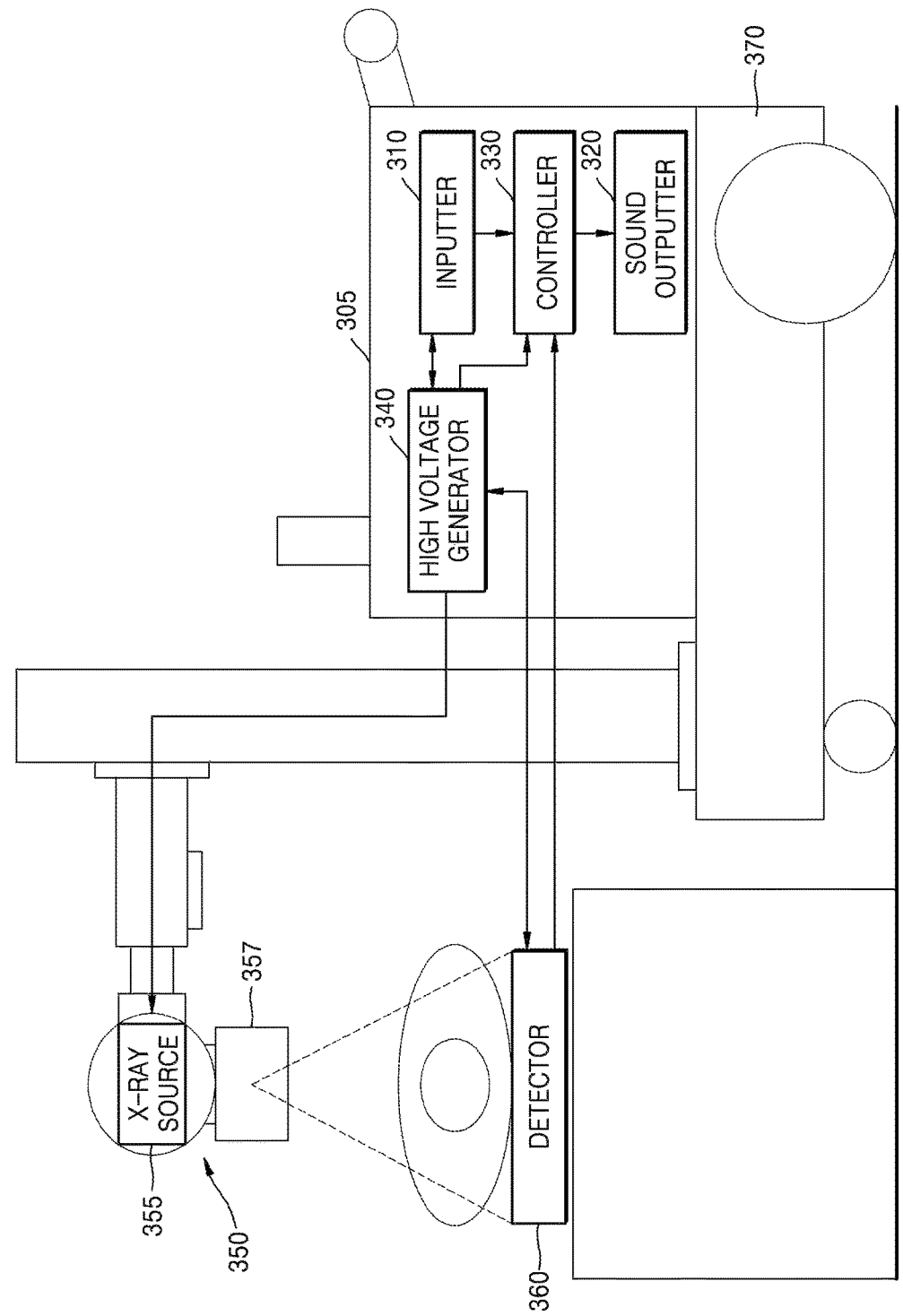
FIG. 3 is a diagram showing a configuration of a mobile X-ray apparatus capable of performing an X-ray photographing operation substantially without limitation as to place according to an exemplary embodiment.

FIG. 3 is a diagram showing a configuration of a mobile X-ray apparatus 300 capable of performing an X-ray photographing operation substantially without limitation as to place according to an exemplary embodiment.

The mobile X-ray apparatus 300 shown in FIG. 3 includes a transport part 370 including a wheel for transporting the X-ray apparatus 300, a main part 305 including an inputter 310 through which commands for operating the X-ray apparatus 300 are input, a high voltage generator 340 for generating a high voltage applied to an X-ray source 355, a sound outputter 320 for outputting sound representing information relating to a photographing operation such as an X-ray irradiation, and a controller 330 for controlling overall operations of the X-ray apparatus 300, an X-ray irradiator 350 including the X-ray source 355 generating the X-ray, and a collimator 357 for guiding a path of the X-ray generated and emitted from the X-ray source 355, and a detector 360 for detecting the X-ray irradiated from the X-ray irradiator 350 and transmitted through an object.

The inputter 310 receives a predetermined input from the user. The inputter 310 may include a keyboard, a mouse, a touch screen, a voice recognizer, a fingerprint recognizer, an iris recognizer, and the like. The user may input a command for irradiating the X-ray via the inputter 310, and the inputter 310 may include a switch for receiving the command input. The switch may be configured to receive the command for irradiating the X-ray when separately manipulated. For example, the switch may receive the command for irradiating the X-ray only when the switch is pushed twice.

That is, in an exemplary embodiment, when the user pushes the switch, a prepare command for performing a pre-heating operation for X-ray irradiation may be input through the switch, and when the user pushes the switch once more, an irradiation command for irradiating the X-ray may be substantially input through the switch. When the user manipulates the switch as described above, the inputter 310 generates signals corresponding to the commands input through the switch manipulation, e.g., a prepare signal and an irradiation signal, and outputs the generated signals to the high voltage generator 340 generating a high voltage for generating the X-ray.

When the high voltage generator 340 receives the prepare signal output from the inputter 310, the high voltage generator 340 starts a pre-heating operation, and when the pre-heating is finished, the high voltage generator 340 outputs a ready signal to the controller 330. In addition, the detector 360 also needs to prepare for detecting the X-ray, and thus, when the high voltage generator 340 receives the prepare signal output from the inputter 310, the high voltage generator 340 outputs the prepare signal to the detector 360 while performing the pre-heating operation, so that the detector 360 may prepare for detecting the X-ray transmitted through the object. The detector 360 prepares for detecting the X-ray in response to the prepare signal, and when the preparing for the detection is finished, the detector 360 outputs a ready signal to the high voltage generator 340 and the controller 330.

When the pre-heating operation of the high voltage generator 340 is finished, the detector 360 is ready for the detecting the X-ray, and the irradiation signal is output from the inputter 310 to the high voltage generator 340, the high voltage generator 340 generates and applies the high voltage to the X-ray source 355, and the X-ray source 355 irradiates the X-ray. When the irradiation signal is output from the inputter 310, the controller 330 may output a sound output signal to the sound outputter 320 so that the sound outputter 320 outputs predetermined sound and the object may recognize the irradiation of X-ray. Also, the sound outputter 320 may output sound representing other information relating to the photographing, in addition to the X-ray irradiation.

In FIG. 3, the sound outputter 320 is included in the main part 305; however, exemplary embodiments are not limited thereto. For example, the sound outputter 320 may be located separately from the mobile X-ray apparatus 300 in a place where the mobile X-ray apparatus 300 is located. For example, the sound outputter 320 may be located on a wall surface of a hospital room in which the mobile X-ray apparatus 300 is located.

The controller 330 controls locations of the X-ray irradiator 350 and the detector 360, a photographing timing, and photographing conditions.

In addition, the controller 330 generates a medical image of the object by using image data transmitted from the detector 360. In particular, the controller 330 receives the image data from the detector 360, and generates the medical image of the object by removing noise in the image data, and adjusting a dynamic range and interleaving of the image data.

The main part 305 of the mobile X-ray apparatus 300 shown in FIG. 3 may further include an outputter (not shown) for outputting the medical image generated by the controller 330. The outputter may output information for allowing the user to manipulate the X-ray apparatus 300, for example, a UI, user information, or object information.

Figure 4:
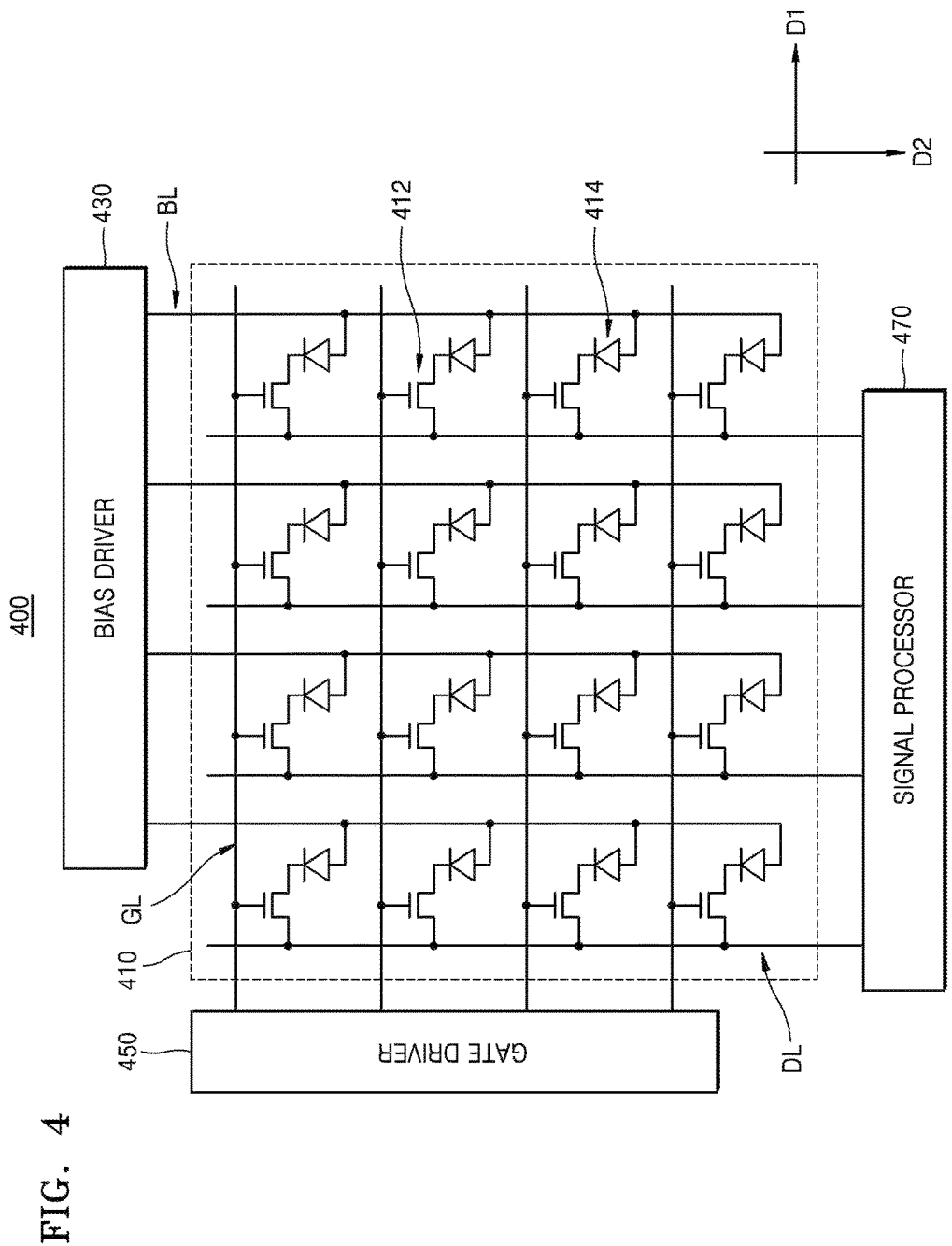
FIG. 4 is a diagram showing a detailed configuration of an indirect type detector according to an exemplary embodiment.

FIG. 4 is a diagram showing a detailed configuration of an indirect type detector 400 according to an exemplary embodiment.

Referring to FIG. 4, the detector 400 may include a scintillator (not shown), a photodetecting substrate 410, a bias driver 430, a gate driver 450, and a signal processor 470.

The scintillator receives the X-ray irradiated from the X-ray source 122 and converts the X-ray into light.

The photodetecting substrate 410 receives the light from the scitillator and converts the light into a photodetecting voltage. The photodetecting substrate 410 may include gate lines GL, data lines DL, thin film transistors (TFTs) 412, photodiodes 414, and bias lines BL.

The gate lines GL may extend in a first direction D1, and the data lines DL may extend in a second direction D2 that substantially crosses the first direction D1. The first direction D1 and the second direction D2 may be substantially perpendicular to each other. FIG. 2 shows four gate lines GL and four data lines DL as an example.

The TFTs 412 may be arranged as a matrix in the first and second directions D1 and D2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 2, sixteen (i.e., 4×4) TFTs 412 are shown as an example.

The photodiodes 414 may be arranged as a matrix in the first and second directions D1 and D2 to correspond to the TFTs 412 in a one-to-one correspondence. Each of the photodiodes 414 may be electrically connected to one of the TFTs 412. An N-side electrode of each of the photodiodes 414 may be electrically connected to a drain of each TFT 412. FIG. 2 shows sixteen (i.e., 4×4) photodiodes 414 as an example.

Each of the photodiodes 414 receives the light from the scintillator and converts the light into the photodetecting voltage. The photodetecting voltage may correspond to an intensity of the X-ray.

The bias lines BL are electrically connected to the photodiodes 414. Each of the bias lines BL may be electrically connected to a P-side electrode of each of the photodiodes 414. For example, the bias lines BL may extend substantially parallel with the second direction D2 to be electrically connected to the photodiodes 414. Alternatively, the bias lines BL may extend substantially parallel with the first direction D1 to be electrically connected to the photodiodes 414. FIG. 2 shows four bias lines BL which extend along the second direction D2 as an example.

The bias driver 430 is electrically connected to the bias lines BL to apply a driving voltage to the bias lines BL. The bias driver 430 may selectively apply a reverse bias or a forward bias to the photodiodes 414 through the bias lines BL. A reference voltage may be applied to the N-side electrode of the photodiode 414. The bias driver 430 may apply a voltage that is less than the reference voltage to the P-side electrode of the photodiode 414 to apply a reverse bias to the photodiode 414. Alternatively, the bias driver 430 may apply a voltage that is greater than the reference voltage to the P-side electrode of the photodiode 414 to apply a forward bias to the photodiode 414.

The gate driver 450 is electrically connected to the gate lines GL to apply gate signals to the gate lines GL. The gate driver 450 sequentially applies the gate signals to the gate lines GL along the second direction D2. For example, when the gate signals are applied to the gate lines GL, the gate signals may turn on the TFTs 412. On the other hand, when the gate signals are not applied to the gate lines GL, the gate signals may turn off the TFTs 412.

The signal processor 470 is electrically connected to the data lines DL to receive sample input voltages from the data lines DL. The signal processor 470 may output image data to the outside by using the sample input voltages. The image data may be an analog signal or a digital signal corresponding to the photodetecting voltage. The signal processor 470 may include one or more hardware and/or software components. For example, the signal processor 470 may include one or more of an integrated circuitry, a dedicated circuit, firmware, and/or a processor such as a central processing unit (CPU) which executes software programs stored in a storage, e.g., a memory.

Although not shown in FIG. 4, when the detector 400 shown in FIG. 4 is a wireless detector, the detector 400 may further include a battery and a wireless communication interface.

A wired detector is associated with a receptor (or tray) of a stand or a table, and thus cannot be moved freely. On the other hand, a wireless detector may be easily moved and thus may be moved from an imaging system currently being used to another imaging system. When a detector is moved to a new imaging system, various information are needed to use the detector in connection with the new imaging system. The various information need to be all stored in the new imaging system. For example, the various information may include an Internet Protocol (IP) address, a type, and a serial number of the detector, and the like.

When the moved detector is not registered in the new imaging system, the moved detector may not be immediately used, and may be used by setting detector information on the new imaging system. In other words, to use a detector not registered in an imaging system, the imaging system needs to be connected to the detector via the IP address of the detector, and the type, serial number, and correction information of the detector need to be informed to the imaging system and stored therein. A process of collecting the information may be included in a process of setting operation conditions of the detector.

According to the related art, to perform detector information setting, a user needs to directly execute an installation program or the like and manually set detector information using the installation program or the like, or needs to acquire information about a detector from another imaging system on a network and set operation conditions of the detector based on the acquired information.

According to an exemplary embodiment, to use a detector not registered in an imaging system during imaging, information about the detector may be acquired from another imaging system, or a user may register the detector in the imaging system by using information stored in the detector without executing a separate installation program, and the operation conditions of the detector may be automatically set on the imaging system.

Figure 5:
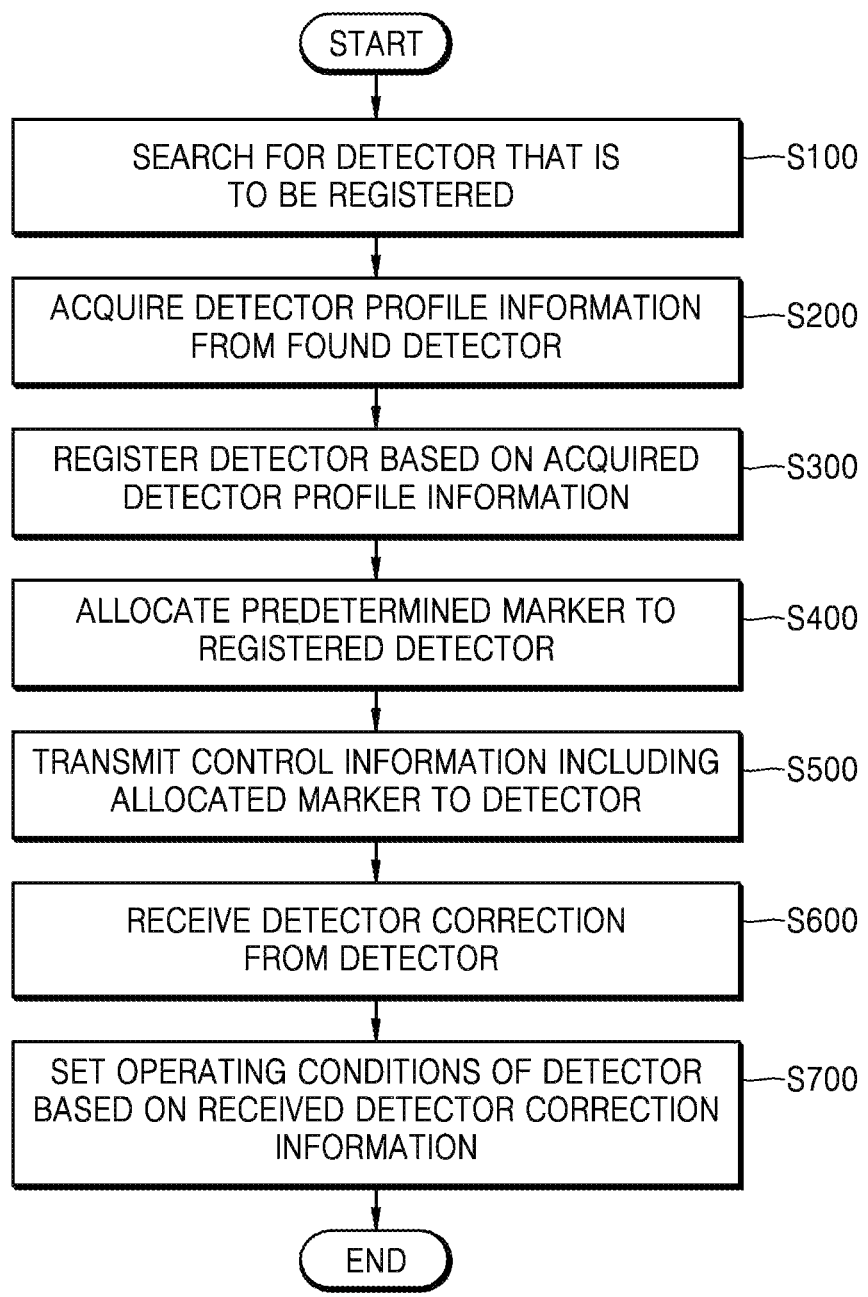
FIG. 5 is a flowchart of a method of setting operating conditions of a detector registered in an imaging system based on detector information pre-stored in the detector according to an exemplary embodiment.

FIG. 5 is a flowchart of a method of setting operation conditions of a detector registered in an imaging system based on detector information pre-stored in the detector according to an exemplary embodiment. FIG. 6 is a flowchart of a method in which an imaging system 1000 and a detector 2000 set operating conditions of the detector 2000 based on detector information according to an exemplary embodiment Referring to FIG. 5, the method may include searching for a detector that is to be registered (S100), acquiring detector profile information from a found detector (S200), registering the detector based on the acquired detector profile information (S300), allocating a predetermined marker to represent activation or non-activation of the registered detector (S400), transmitting control information including the allocated marker to the detector (S500), receiving detector correction information from the detector (S600), and setting operating conditions of the detector based on the received detector correction information (S700). The detector information may include the detector profile information and the detector correction information.

Referring to FIG. 6, the imaging system 1000 according to an exemplary embodiment may be included in a workstation. Alternatively, the imaging system 1000 may exist separately from the workstation.

Operations S100 to S700 in FIG. 6 are substantially the same or similar to those described above with respect to FIG. 5 and thus any repetitive explanation will be omitted.

Operation S100 of searching for a detector to be registered may include searching for a virtual IP address of the detector 2000, which is to be registered (S110) and accessing the detector 2000 via a found virtual IP address (S120).

A detector according to an exemplary embodiment may be allocated a real IP address and a virtual IP address for each media access control (MAC) address. A real IP address may be uniquely allocated to each detector, and an identical virtual IP address may be allocated to a plurality of detectors. In other words, different real IP addresses may be allocated to different detectors, and an identical virtual IP address may be allocated to a plurality of detectors.

The imaging system 1000 may perform data communications with a detector already registered on the imaging system 1000 via a real IP address, and may determine, via a virtual IP address, whether a detector currently not registered on the imaging system 1000 exists. The imaging system 1000 may access the to-be-registered detector 2000 via the found virtual IP address.

After accessing the detector 2000, the imaging system 1000 may acquire detector profile information from the detector 2000. For example, the imaging system 1000 may receive the detector profile information from the detector 2000 via the virtual IP address. The detector profile information may include at least one of a real IP address, a type, and a serial number of the detector 2000.

Operation S300 of registering a detector may include storing the detector profile information on a candidate detector list to an available detector list on the imaging system 1000.

A predetermined marker according to an exemplary embodiment may include at least one of a character, a number, a symbol, a color, and an image.

Referring back to FIG. 5, a predetermined marker may be allocated to the detector 2000 registered in the imaging system 1000 (S400). The imaging system 1000 may allocate the predetermined marker to the registered detector 2000 so that the allocated marker is used as an identifier of the detector 2000.

The control information including the allocated marker may be transmitted to the detector 2000 (S500).

The imaging system 1000 may receive the detector correction information from the detector 2000 (S600). Operation S600 of receiving the detector correction information from the detector 2000 may include receiving the detector correction information from the detector 2000 via an access to an activated real IP address of the detector 2000. For example, since the detector 2000 switches from a virtual IP address to a real IP address in response to the control information including the allocated marker and transmits the detector correction information to the imaging system 1000 via the real IP address, the imaging system 1000 may receive the detector correction information from the detector 2000.

The operating conditions of the detector 2000 may be set based on the received detector correction information (S700). Operation S700 of setting the operating conditions of the detector 2000 may include setting imaging conditions for performing imaging using the detector 2000, based on the detector correction information received from the detector 2000.

For example, the operating conditions of the detector 2000 may be referred to as an operating environment of the detector 2000 when X-ray imaging is being performed using the detector 2000, such as, an amount of step difference correction of the detector 2000 during imaging and a range of defective pixel compensation.

In this case, the detector correction information may include at least one of detector step difference correction information and defective pixel compensation information. As described above, the detector information may include the detector profile information and the detector correction information.

Figure 7A:
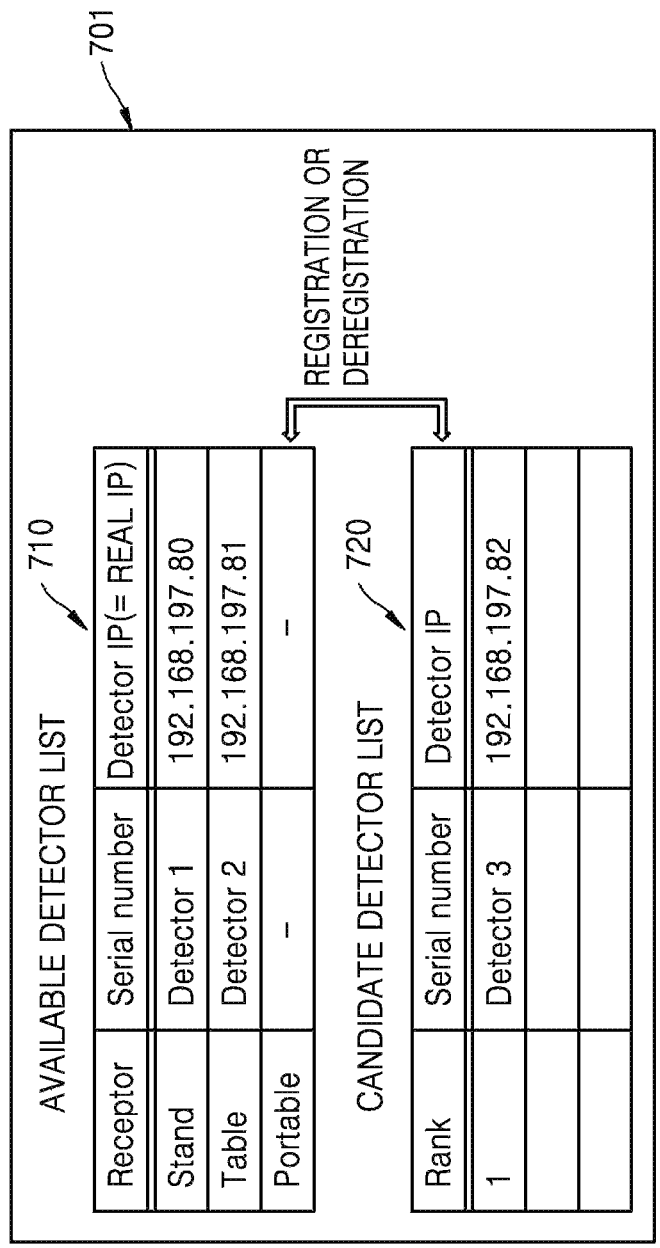
FIG. 7A illustrates an image displayed on an imaging system, which includes an available detector list and a candidate detector list according to an exemplary embodiment.
Figure 7B:
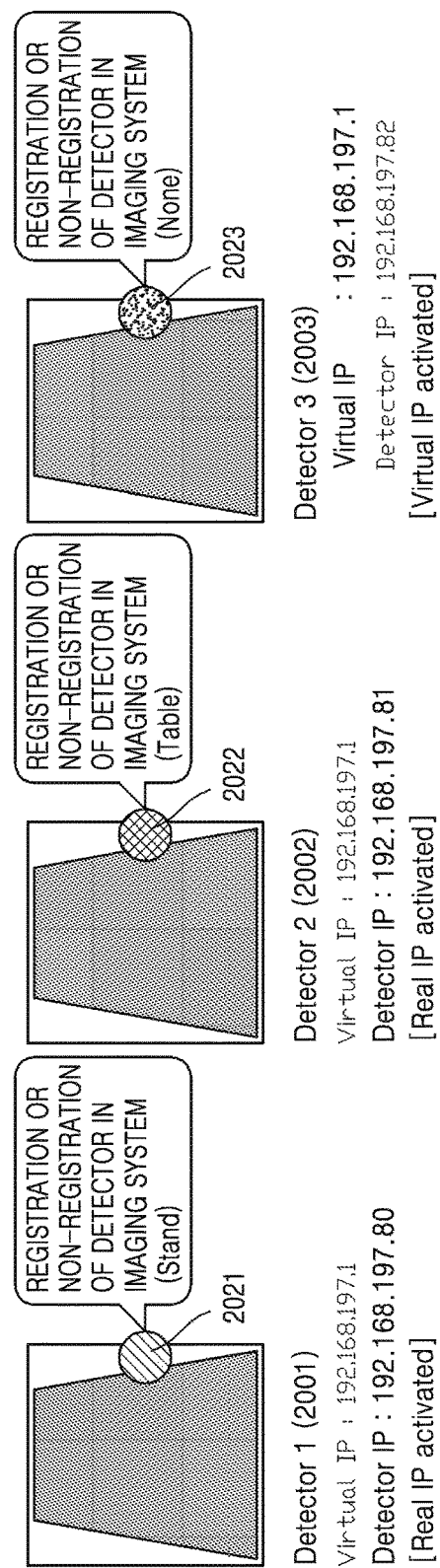
FIG. 7B illustrates an image displayed on an imaging system, which includes information on detectors according to an exemplary embodiment.

FIG. 7A illustrates an image 701 of the imaging system 1000 including an available detector list 710 and a candidate detector list 720 according to an exemplary embodiment. FIG. 7B illustrates an image displayed on an imaging system, which includes information on detectors according to an exemplary embodiment.

As illustrated in FIG. 7A, a display (not shown) of the imaging system 1000 may display the image 701, which includes the available detector list 710 and the candidate detector list 720.

The available detector list 710 includes information about at least one detector currently registered (or identified) on the imaging system 1000. The candidate detector list 720 includes information about at least one detector not yet registered on the imaging system 1000.

As described above, the detector profile information of the to-be-registered detector acquired via the virtual IP address may be displayed to a user in the form of the candidate detector list 720. A detector may be registered in the imaging system 1000 by storing, in the available detector list 710, the detector profile information of the detector displayed on the candidate detector list 720.

In addition, a predetermined detector may be deregistered from the imaging system 1000, based on a user input via an external input receiver (not shown) or the like that may be connected to the imaging system 1000. When a detector is deregistered, information about the deregistered detector may be deleted from the available detector list 710. The information deleted from the available detector list 710 may be included in the candidate detector list 720, or may also be deleted from the candidate detector list 720.

As illustrated in FIGS. 7A and 7B, with respect to a detector 2001 or 2002 registered in the imaging system 1000, real IP address thereof may be activated. For example, the real IP address of the detector 2001, namely, 192.168.197.80, may be activated so that the detector 2001 may communicate with the imaging system 1000. The real IP address of the detector 2002, namely, 192.168.197.81, may be activated so that the detector 2002 may communicate with the imaging system 1000.

The detector 2001 or 2002 may display a registration or non-registration status thereof in the imaging system 1000 by using an allocated marker 2021 or 2022. For example, the allocated marker 2021 or 2022 may be displayed in a predetermined pattern via a display of the detector 2001 or 2002. For example, the predetermined pattern may include a pattern in which at least one of, for example, a size, a position, and a color of the allocated marker 2021 or 2022 is changed during a predetermined period of time, a pattern in which the allocated marker 2021 or 2022 flickers during a predetermined period of time, or any other patterns. When a predetermined color, e.g., a yellow color is allocated to the detector 2001 registered in the imaging system 1000, the detector 2001 may display the marker 2021 in the yellow color on the display. When a predetermined color, e.g., a violet color is allocated to the detector 2002 registered in the imaging system 1000, the detector 2002 may display the marker 2022 in the violet color on the display. In other words, the detector 2001 or 2002 registered in the imaging system 1000 may display registration or non-registration thereof in the imaging system 1000 by using the allocated marker 2021 or 2022.

With respect to a detector 2003 not yet registered in the imaging system 1000, a virtual IP address thereof may be activated. For example, the virtual IP address of the detector 2003, namely, 192.168.197.1, may be activated so that the detector 2003 may communicate with the imaging system 1000. In other words, the imaging system 1000 may search for the unregistered detector 2003 by searching for the virtual IP address of the unregistered detector 2003.

The detector 2003 not yet registered in the imaging system 1000 may not display any marker or may display a marker 2023 for indicating non-registration of the detector 2003. For example, the marker 2023 may comprise a marker for alarming, which may be a red light or the like.

Referring back to FIG. 6, a method of transmitting detector correction information of the detector 2000 to the imaging system 1000 in which the detector 2000 has been registered based on the detector information pre-stored in the detector 2000 according to an exemplary embodiment may include receiving an access request for accessing the detector 2000 via the virtual IP address from the imaging system 1000 (S1000), transmitting the detector profile information to the imaging system 1000 (S2000), receiving first control information including an allocated predetermined marker from the imaging system 1000 (S3000), switching the IP address of the detector 2000 based on the received first control information (S4000), and transmitting the detector correction information to the imaging system 1000 in response to a detector correction information transmission request from the imaging system 1000 (S5000). The detector information may include the detector profile information and the detector correction information.

The detector profile information may include at least one of a real IP address, a type, and a serial number of the detector 2000. The predetermined marker may include at least one of a character, a number, a symbol, a color, and an image. The detector correction information may include at least one of detector step difference correction information and defective pixel compensation information.

Operation S4000 of switching the IP address of the detector 2000 based on the received first control information may include deactivating the virtual IP address of the detector 2000 and activating the real IP address thereof, and displaying a state change of the detector 2000 by using the received predetermined marker.

The method of transmitting the detector correction information of the detector 2000 to the imaging system 1000 in which the detector 2000 has been registered based on the detector information pre-stored in the detector 2000 may further include receiving second control information from the imaging system 1000 (S6000), deactivating the real IP address and activating the virtual IP address based on the second control information (S7000), and changing the marker to display a change of the state of the detector (S8000).

As described above with reference to operation S500, the imaging system 1000 may transmit the control information to the detector 2000. The control information transmitted in operation S500 may include the first control information and the second control information. Alternatively, the control information transmitted in operation S500 may include the first control information and the control information transmitted in operation S800 may include the second control information.

For example, the second control information may include a command or the like for deregistering the detector 2000. In response to the second control information transmitted at operation S800, the detector 2000 may switch an IP address thereof (S7000). For example, when the detector 2000 of which the real IP address has been activated and the virtual IP address has been deactivated receives the second control information including, for example, a command for deregistering the detector 2000, the detector 2000 may deactivate the real IP address and activate the virtual IP address.

FIG. 8 is a flowchart of a method in which the imaging system 1000 and the detector 2000 set operating conditions of the detector 2000 based on detector information according to another exemplary embodiment.

Referring to FIG. 8, operation S100 of searching for a detector 2000 that is to be registered may include determining existence or absence of detector profile information that is being broadcast on a wired or wireless network including the imaging system 1000 (S130) and accessing the detector 2000 that is not yet registered and corresponds to the detector profile information that is being broadcast on the wired or wireless network (S140).

The detector 2000 not yet registered in the imaging system 1000 may broadcast the detector profile information to different devices (e.g., another imaging system or another detector) via the wired or wireless network including the imaging system 1000 and the detector 2000. On the other hand, a detector already registered in the imaging system 1000 may perform unicast communications with the imaging system 1000.

The imaging system 1000 may determine existence or absence of detector profile information that is being broadcast, and determine existence or absence of an unregistered detector according to the determination of existence or absence of detector profile information.

When the detector profile information being broadcast exists, the imaging system 1000 may determine that an unregistered detector exists on the wired or wireless network including the imaging system 1000. On the other hand, when the detector profile information being broadcast does not exist, the imaging system 1000 may determine that no unregistered detectors exists on the wired or wireless network including the imaging system 1000, and may continue the operation S100 of searching for a detector that is to be registered.

When it is determined in operation S130 that the detector profile information being broadcast exists, the imaging system 1000 may access the detector 200 corresponding to the broadcast detector profile information (S140).

Operation S200 of acquiring the detector profile information may include receiving the broadcast detector profile information from the detector 2000 that is not yet registered (S210) and storing the detector profile information in a candidate detector list (S220). The detector profile information may include at least one of a real IP address, a type, and a serial number of the detector 2000.

Operation S300 of registering the detector 2000 may include storing the detector profile information on the candidate detector list to an available detector list on the imaging system 1000.

After a predetermined marker is allocated to the detector 2000 (S400) and control information including the allocated marker is transmitted to the detector 2000 (S500), the imaging system 1000 may receive detector correction information from the detector 2000 (S600).

Operation S600 of receiving the detector correction information from the detector 2000 may include receiving detector correction information from the detector 2000 of which the detector profile information has been stored in the available detector list in the detector registration operation S300. Operation S700 of setting the operating conditions of the detector 2000 may include setting imaging conditions for performing imaging using the detector 2000, based on the received detector correction information. The detector correction information may include at least one of detector step difference correction information and defective pixel compensation information.

A method of transmitting the detector correction information of the detector 2000 to the imaging system 1000 in which the detector 2000 has been registered based on the detector information pre-stored in the detector 2000 according to an exemplary embodiment may include broadcasting the detector profile information to the wired or wireless network including the imaging system 1000 (S900), receiving first control information including an allocated predetermined marker from the imaging system 1000 (S3000), stopping the broadcasting by the detector 2000 based on the received first control information (S4100), and transmitting the detector correction information to the imaging system 1000 in response to a detector correction information transmission request from the imaging system 1000 (S5000). The detector information may include the detector profile information and the detector correction information.

The method of transmitting the detector correction information of the detector 2000 to the imaging system 1000 in which the detector 2000 has been registered based on the detector information pre-stored in the detector 2000 may further include receiving an access request from the imaging system 1000 (S1000) and transmitting the detector profile information to the imaging system 1000 (S2000).

Operation S4100 of stopping the broadcasting by the detector 2000 based on the received first control information may include displaying a change of the state of the detector 2000 by using the received predetermined marker.

The method of transmitting the detector correction information to the imaging system 1000 based on the detector information pre-stored in the detector 2000 may further include receiving second control information from the imaging system 1000 (S6000), starting the broadcasting of the detector profile information to the wired or wireless network based on the received second control information (S7100), and changing the marker to display a change of the state of the detector 2000 (S8000).

Figure 9:
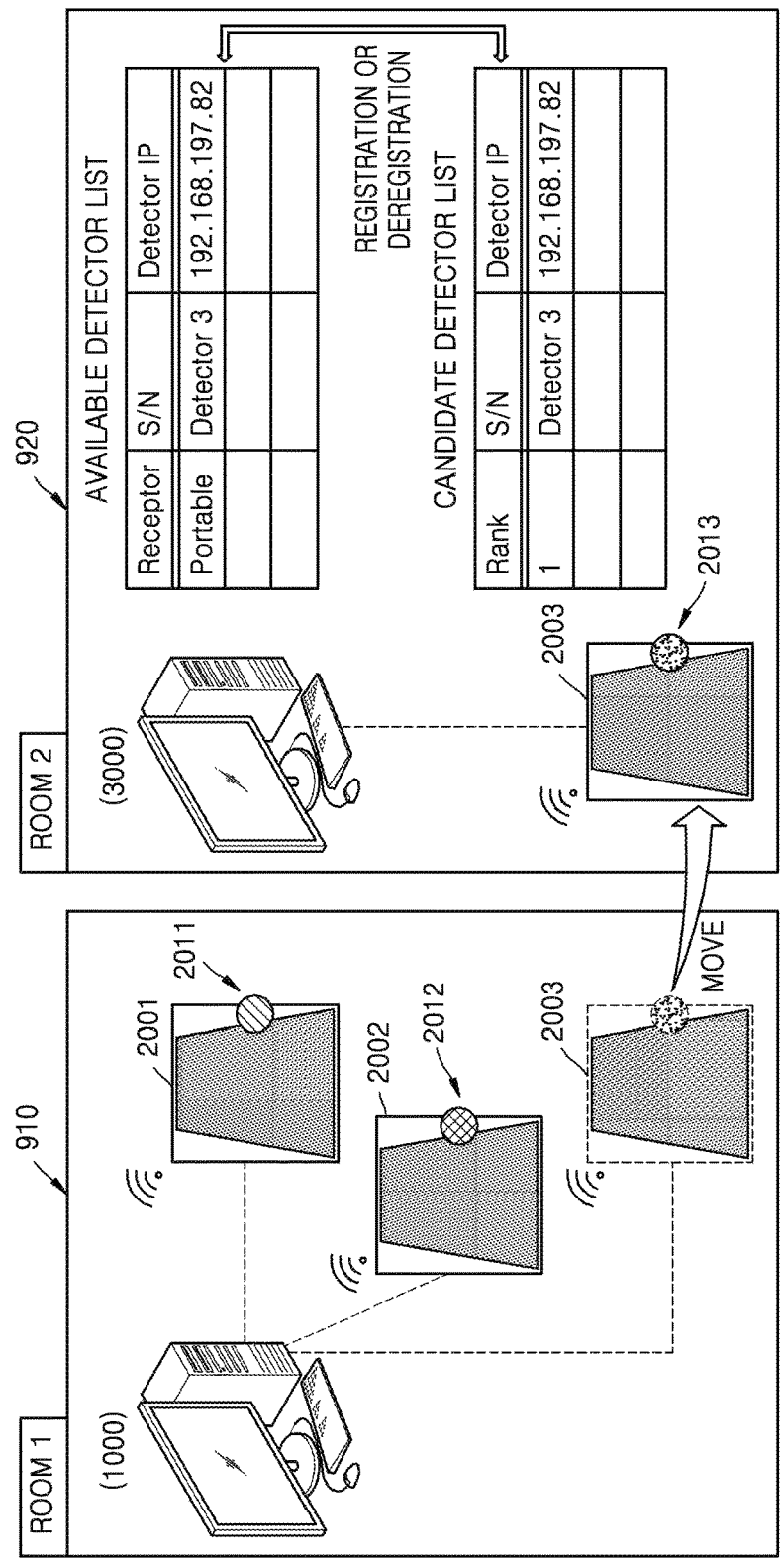
FIG. 9 illustrates registration of a detector in an imaging system based on detector information pre-stored in the detector when the detector moves into another location according to an exemplary embodiment.

FIG. 9 illustrates registration of a detector in an imaging system based on detector information pre-stored in the detector when the detector moves into another location according to an exemplary embodiment.

For example, the second control information may be transmitted to a detector 2003 that has been registered in and used in the imaging system 1000 of a first imaging space 910 (or room 1) so that the detector 2003 may be deregistered. When the detector 2003 is deregistered, the imaging system 1000 may not access the detector 2003 via the real IP address and may only access the detector 2003 via the virtual IP address. Due to the deregistration of the detector 2003, the state of the detector 2003 is changed, and thus the detector 2003 may display a predetermined marker in a predetermined pattern. For example, on a display 2013 of the detector 2003, a red light may flicker at time intervals of, for example, one or two seconds to represent the deregistration of the detector 2003.

When a user moves the detector 2003 to a second imaging space 920 (or room 2), an imaging system 3000 of the second imaging space 920 (or room 2) may perform operation S100 of searching for a to-be-registered detector, to determine whether a detector to be registered exists within the second imaging space 920. In other words, the imaging system 3000 may search for a detector that is accessible via a virtual IP address thereof.

The imaging system 3000 of the second imaging space 920 acquires detector profile information from a found detector, namely, the detector 2003, and registers the found detector 2003. When the detector 2003 is registered in the imaging system 3000 of the second imaging space 920, the real IP address of the detector 2003 may be activated, and the virtual IP address thereof may be deactivated. Due to the registration of the detector 2003, the activation state of the IP address of the detector 2003 is changed, and thus the detector 2003 may display a predetermined marker in a predetermined pattern. For example, a blue light is turned on, on the display 2013 of the detector 2003.

The imaging system 3000 of the second imaging space 920 may allocate a predetermined marker to the detector 2003, transmit control information including the allocated marker to the detector 2003, and receive detector correction information from the detector 2003.

The imaging system 3000 of the second imaging space 920 may set operating conditions of the detector 2003 within the second imaging space 920, based on the received detector correction information. The set operating conditions may be stored in a storage (not shown) included in the imaging system 3000. Alternatively, the set operating conditions may exist separately from the imaging system 3000 and may be stored in a storage (not shown) connected to the imaging system 3000.

According to another example, the second control information may be transmitted to the detector 2003 that has been registered and used in the imaging system 1000 of the first imaging space 910 (or room 1) so that the detector 2003 may be deregistered. The detector deregistered from the imaging system 1000 of the first imaging space 910 may broadcast the detector profile information to the wired or wireless network. For example, the detector 2003 may broadcast the detector profile information to other devices existing on the wired or wireless network, via an IP address for broadcasting.

Due to the deregistration of the detector 2003, the state of the detector 2003 is changed, and thus the detector 2003 may display a predetermined marker in a predetermined pattern. For example, on the display 2013 of the detector 2003, a red light may flicker at time intervals of one or two seconds to represent the deregistration of the detector 2003.

When a user moves the detector 2003 to the second imaging space 920 (or room 2), the imaging system 3000 of the second imaging space 920 may determine whether detector profile information being broadcast on the wired or wireless network exists, and may access a detector that exists on the wired or wireless network and broadcasts the detector profile information thereof. In other words, the imaging system 3000 of the second imaging space 920 may perform operation S100 of searching for a to-be-registered detector, to determine whether a detector that broadcasts the detector profile information exists on the wired or wireless network.

The imaging system 3000 of the second imaging space 920 acquires detector profile information from a found detector, namely, the detector 2003, and registers the detector 2003. When the detector 2003 is registered in the imaging system 3000 of the second imaging space 920, the broadcasting of the detector profile information by the detector 2003 may be stopped.

To represent the stoppage of the broadcasting by the detector 2003, the detector 2003 may display a predetermined marker in a predetermined pattern. For example, a blue light is turned on, on the display 2013 of the detector 2003.

The imaging system 3000 of the second imaging space 920 may allocate a predetermined marker to the detector 2003, transmit control information including the allocated marker to the detector 2003, and receive detector correction information from the detector 2003.

The imaging system 3000 of the second imaging space 920 may set operating conditions of the detector 2003 within the second imaging space 920, based on the received detector correction information. The set operating conditions may be stored in the storage (not shown) included in the imaging system 3000. Alternatively, the set operating conditions may exist separately from the imaging system 3000 and may be stored in a storage (not shown) connected to the imaging system 3000.

Figure 10:
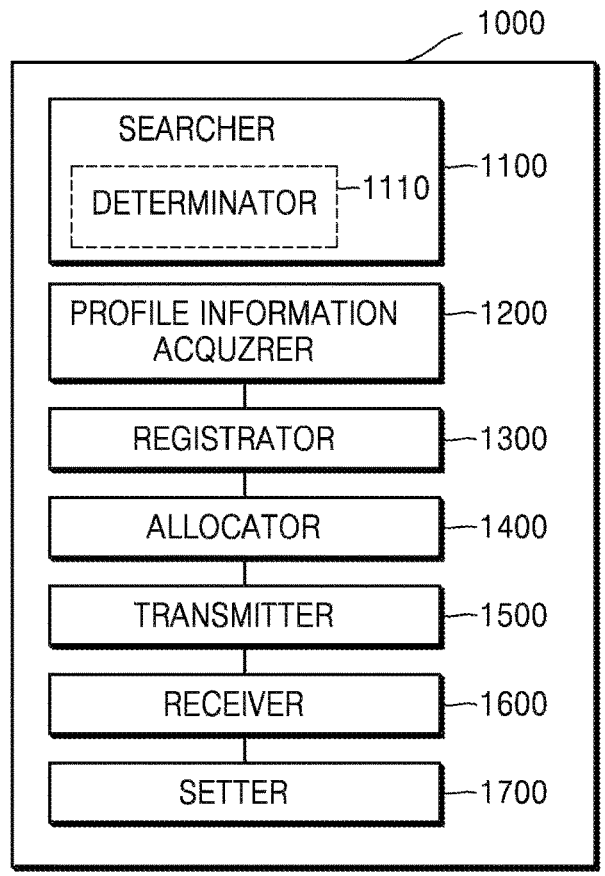
FIG. 10 is a block diagram of an imaging system for setting operating conditions of a detector registered in the imaging system based on detector information pre-stored in the detector according to an exemplary embodiment.

FIG. 10 is a block diagram of an imaging system 1000 for setting operation conditions of a detector registered in the imaging system 1000 based on detector information pre-stored in the detector according to an exemplary embodiment.

Referring to FIG. 10, the imaging system 1000 may include a searcher 1100 which searches for a detector that is to be registered, a profile information acquirer 1200 which acquires detector profile information from a found detector, a registrator 1300 which registers the detector based on the acquired detector profile information, an allocator 1400 which allocates a predetermined marker to represent activation or non-activation of the registered detector, a transmitter 1500 which transmits control information including the allocated marker to the detector, a receiver 1600 which receives detector correction information from the detector, and a setter 1700 which sets operating conditions of the detector based on the received detector correction information.

The detector information may include, for example, the detector profile information and the detector correction information.

The searcher 1100 may search for a virtual IP address of the detector that is to be registered, and may access the detector that is to be registered via a found virtual IP address.

The detector profile information may include at least one of the real IP address of the detector, the type thereof, and the serial number thereof, and the registrator 1300 may store the detector profile information on a candidate detector list to an available detector list on the imaging system 1000. The detector profile information may be stored in a storage (not shown) included in the imaging system 1000. Alternatively, the detector profile information may exist separately from the imaging system 1000, but may be stored in a storage (not shown) connected to the imaging system 1000.

The predetermined marker may include at least one of a character, a number, a symbol, a color, and an image.

The receiver 1600 may receive the detector correction information from the detector by accessing an activated real IP address of the detector. The setter 1700 may set imaging conditions for performing imaging using the detector, based on the detector correction information received from the detector. The detector correction information may include at least one of detector step difference correction information and defective pixel compensation information.

The searcher 1100 may further include a determinator 1110 which determines whether detector profile information being broadcast on a wired or wireless network including the imaging system exists. The searcher 1100 may access an unregistered detector corresponding to the detector profile information that is being broadcast on the wired or wireless network.

The profile information acquirer 1200 may receive the detector profile information from the unregistered detector and may store the detector profile information in a candidate detector list. The detector profile information may include at least one of the real IP address of the detector, the type thereof, and the serial number thereof.

The registrator 1300 may store the detector profile information on the candidate detector list to an available detector list on the imaging system 1000.

The receiver 1600 may receive detector correction information from the detector of which the detector profile information has been stored in the available detector list. The setter 1700 may set imaging conditions for performing imaging using the detector, based on the received detector correction information. The detector correction information may include at least one of detector step difference correction information and defective pixel compensation information.

One or more of the above elements 1100 to 1700 may be implemented with at least one processor module. For example, one or more of the above elements 1100 to 1700 may be implemented as an array of a plurality of logic gates, or may be implemented as a combination of a general-use microprocessor and a memory that stores a program executable by the microprocessor. Also, one or more of the above elements 1100 to 1700 may be implemented as an application program module.

Figure 11:
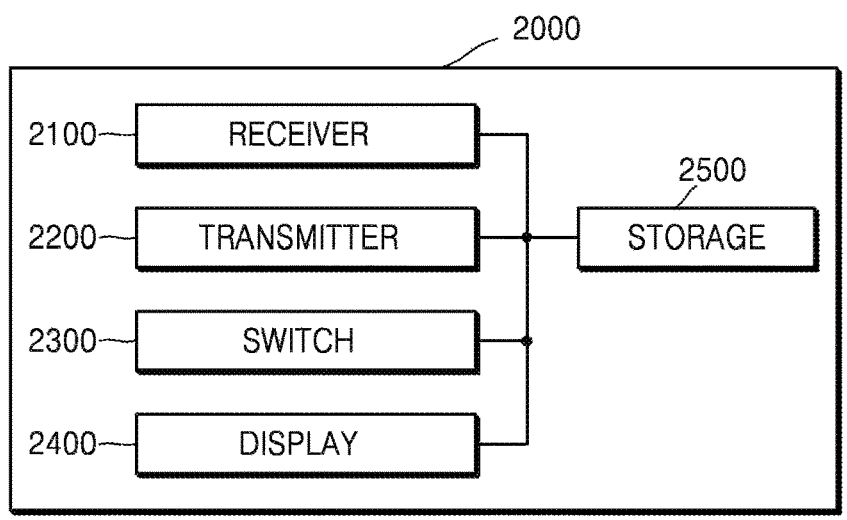
FIG. 11 is a block diagram of a detector for transmitting detector correction information to an imaging system in which the detector has been registered based on detector information pre-stored in the detector according to an exemplary embodiment.

FIG. 11 is a block diagram of a detector 2000 for transmitting detector correction information to an imaging system in which the detector 2000 has been registered based on detector information pre-stored in the detector 2000 according to an exemplary embodiment.

Referring to FIG. 11, the detector 2000 may include a receiver 2100 which receives an access request for accessing the detector 2000 via a virtual IP address from the imaging system, and a transmitter 2200 which transmits detector profile information of the registered detector 2000 to the imaging system. The receiver 2100 may receive first control information including a predetermined marker, from the imaging system. The detector 2000 may further include a switch 2300 which switches the IP address of the detector 2000 based on the received first control information. The transmitter 2200 may also transmit detector correction information to the imaging system, in response to a detector correction information transmission request from the imaging system. The detector information may include the detector profile information and the detector correction information.

The detector 2000 may further include a storage 2500 which stores the detector profile information, the marker, or the detector correction information.

The detector profile information may include, for example, at least one of the real IP address of the detector 2000, the type thereof, and the serial number thereof. The marker may include, for example, at least one of a character, a number, a symbol, a color, and an image. The detector correction information may include, for example, at least one of detector step difference correction information and defective pixel compensation information.

The switch 2300 may deactivate the virtual IP address of the detector 2000 and activate the real IP address of the detector 2000. The detector 2000 may further include a display 2400 which displays a change of the state of the detector 2000 by using a received predetermined marker.

The receiver 2100 may receive second control information from the imaging system, and the switch 2300 may deactivate the real IP address of the detector 2000 and activate the virtual IP address of the detector 2000, based on the received second control information.

The display 2400 may display a change of the state of the detector 2000 by changing the received marker.

One or more of the above elements 2100 to 2500 may be implemented with at least one processor module. For example, one or more of the above elements 2100 to 2500 may be implemented as an array of a plurality of logic gates, or may be implemented as a combination of a general-use microprocessor and a memory that stores a program executable by the microprocessor. Also, one or more of the above elements 2100 to 2500 may be implemented as an application program module.

Figure 12:
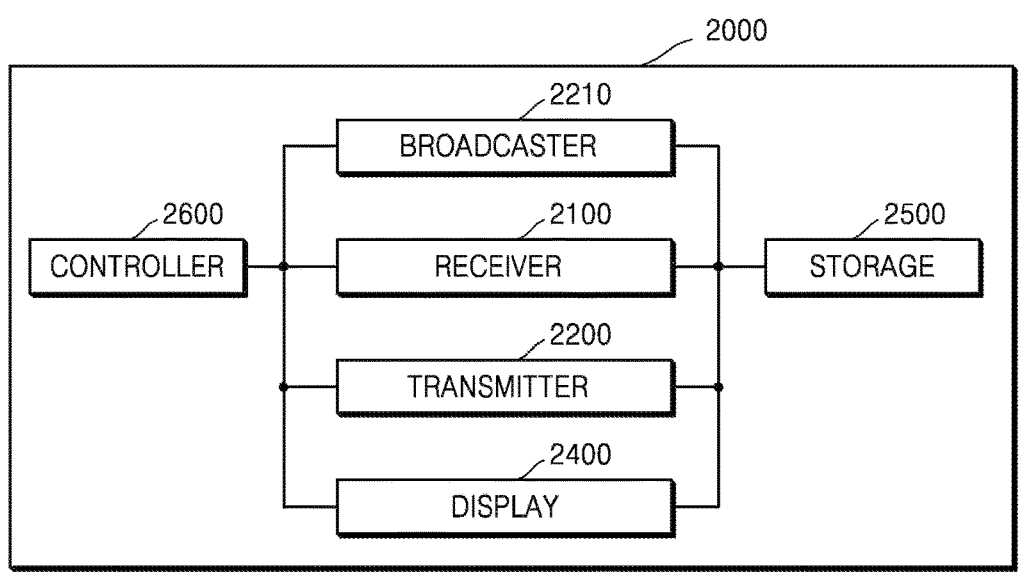
FIG. 12 is a block diagram of a detector for transmitting detector correction information to an imaging system in which the detector has been registered based on detector information pre-stored in the detector according to another exemplary embodiment.

FIG. 12 is a block diagram of a detector 2000 for transmitting detector correction information to an imaging system in which the detector 2000 has been registered based on detector information pre-stored in the detector 2000 according to another exemplary embodiment.

Referring to FIG. 12, the detector 2000 may include a broadcaster 2210 which broadcasts detector profile information of the detector 2000 to a wired or wireless network including the imaging system, a receiver 2100 which receives first control information including an allocated predetermined marker from the imaging system, a controller 2600 which stops the broadcasting by the detector 2000 based on the received first control information, and a transmitter 2200 which transmits the detector correction information to the imaging system in response to a detector correction information transmission request from the imaging system. The detector information may include the detector profile information and the detector correction information.

The detector 2000 may further include a display 2400 which displays a change of the state of the detector 2000 by using a received predetermined marker when the broadcasting by the detector 2000 is stopped by the controller 2600.

The controller 2600 may include one or more hardware and/or software components. For example, the controller 2600 may include one or more of an integrated circuitry, a dedicated circuit, firmware, and/or a processor such as a central processing unit (CPU) which executes software programs stored in a storage, e.g., a memory.

The detector 2000 may further include a storage 2500 which stores the detector profile information, the marker, or the detector correction information.

The receiver 2100 may receive second control information from the imaging system, and the broadcaster 2210 may start broadcasting of detector profile information to the wired or wireless network, based on the received second control information. The display 2400 may display a change of the state of the detector 2000 by changing the marker.

The above-described methods according to exemplary embodiments may be applied to the imaging system 1000 of FIG. 10 and the detectors 2000 of FIGS. 11 and 12. Therefore, any repetitive explanation of the imaging system 1000 and the detectors 2000 will be omitted.

Exemplary embodiments may also be implemented through computer-readable recording media having recorded thereon computer-executable instructions such as program modules that are executed by a computer, which include at least one processor. Computer-readable media may be any available media that can be accessed by a computer and include both volatile and nonvolatile media and both detachable and non-detachable media. Examples of the computer-readable media may include a read-only memory (ROM), a random-access memory (RAM), a compact disc (CD)-ROM, a magnetic tape, a floppy disk, an optical data storage device, etc. Furthermore, the computer-readable media may include computer storage media and communication media. The computer storage media include both volatile and nonvolatile and both detachable and non-detachable media implemented by any method or technique for storing information such as computer-readable instructions, data structures, program modules or other data. The communication media typically embody computer-readable instructions, data structures, program modules, other data of a modulated data signal such as a carrier wave, or other transmission mechanism, and they include any information transmission media.

While the exemplary embodiments have been particularly shown and described with reference to exemplary embodiments thereof, it will be understood by those of ordinary skill in the art that various changes in form and details may be made therein without departing from the spirit and scope as defined by the following claims.

What is claimed is:

1. A method of setting operation conditions of a detector in an X-ray imaging system, the method comprising:
   searching for a virtual IP address of the detector that is not registered in the X-ray imaging system;
   acquiring detector profile information based on the virtual IP address;
   registering the detector based on the detector profile information, the detector profile information comprising a real IP address of the detector;
   receiving detector correction information from the detector via an access to the real IP address of the detector; and
   setting operation conditions of the detector based on the received detector correction information,
   wherein the registering comprises transmitting first control information for activating the real IP address of the detector and deactivating the virtual IP address of the detector.

2. The method of claim 1, wherein the registering comprises:
   allocating a predetermined marker to the registered detector to represent activation or non-activation thereof; and
   transmitting the first control information including the allocated predetermined marker to the detector.

3. The method of claim 1, wherein
   the detector profile information further comprises at least one from among a type and a serial number of the detector, and
   the registering comprises storing the detector profile information to an available detector list of the X-ray imaging system.

4. The method of claim 3, wherein
   the setting comprises setting operation conditions for performing imaging using the detector based on the detector correction information, and
   the detector correction information comprises at least one from among detector step difference correction information indicating an amount of step difference correction of the detector for performing imaging and defective pixel compensation information indicating a range of defective pixel compensation of the detector for performing imaging.

5. The method of claim 2, wherein the allocated predetermined marker comprises at least one from among a character, a number, a symbol, a color, and an image.

6. The method of claim 1, wherein
   the searching comprises:
      determining whether the detector profile information is broadcast on a network to which the X-ray imaging system is connected; and
      accessing an unregistered detector corresponding to the detector profile information that is being broadcast on the network,
   the acquiring comprises:
      receiving the broadcast detector profile information from the unregistered detector; and
      storing the detector profile information in a candidate detector list, and
   the detector profile information further comprises at least one from among a type and a serial number of the unregistered detector.

7. The method of claim 6, wherein the registering comprises storing the detector profile information on the candidate detector list to an available detector list of the X-ray imaging system.

8. The method of claim 7, wherein
   the receiving comprises receiving the detector correction information from the detector having the detector profile information stored in the available detector list,
   the setting comprises setting operation conditions for performing imaging using the detector based on the detector correction information, and
   the detector correction information comprises at least one from among detector step difference correction information indicating an amount of step difference correction of the detector for performing imaging and defective pixel compensation information indicating a range of defective pixel compensation of the detector for performing imaging.

9. A method of transmitting detector correction information of a detector to an X-ray imaging system, the method comprising:
receiving, from the X-ray imaging system, a request to access the detector via a virtual IP address of the detector;
transmitting detector profile information of the detector to the X-ray imaging system in response to the request, the detector profile information comprising a real IP address of the detector;
receiving, from the X-ray imaging system, first control information;
deactivating the virtual IP address of the detector and activating the real IP address of the detector based on the first control information; and
transmitting the detector correction information to the X-ray imaging system.

10. The method of claim 9, wherein the detector profile information comprises at least one from among a type and a serial number of the detector, and
wherein the detector correction information comprises at least one from among detector step difference correction information indicating an amount of step difference correction of the detector for performing imaging and defective pixel compensation information indicating a range of defective pixel compensation of the detector for performing imaging.

11. The method of claim 9, wherein the first control information includes an allocated predetermined marker to the detector,
wherein the allocated predetermined marker comprises at least one from among a character, a number, a symbol, a color, and an image, and
wherein the method further comprises displaying a change of a state of the detector by using the allocated predetermined marker.

12. The method of claim 11, further comprising:
receiving second control information from the X-ray imaging system;
deactivating the real IP address of the detector and activating the virtual IP address of the detector based on the second control information; and
displaying the change of the state of the detector by using the allocated predetermined marker.

13. A method of transmitting detector correction information of a detector to an X-ray imaging system, the method comprising:
broadcasting detector profile information to a network to which the X-ray imaging system is connected;
receiving, from the X-ray imaging system, first control information; and
stopping the broadcasting based on the first control information; and transmitting, from the detector, the detector correction information to the X-ray imaging system based on the first control information.

14. The method of claim 13, wherein the first control information includes an allocated predetermined marker, and wherein the stopping comprises displaying a change of a state of the detector by using the allocated predetermined marker.

15. The method of claim 14, further comprising:
receiving second control information from the X-ray imaging system;

starting broadcasting of the detector profile information to the network based on the second control information; and
displaying the change of the state of the detector by using the allocated predetermined marker.

16. An X-ray imaging system for setting operation conditions of a detector, the X-ray imaging system comprising:
a memory;
a controller configured to search for a virtual IP address of the detector that is not registered in the X-ray imaging system, acquire detector profile information about the detector based on the virtual IP address, register the detector based on the detector profile information, the detector profile information comprising a real IP address of the detector; and
a communicator configured to transmit first control information for activating the real IP address of the detector and deactivating the virtual IP address of the detector to the detector, and receive detector correction information from the detector via an access to the real IP address of the detector,
wherein the controller further configured to set operation conditions of the detector based on the received detector correction information.

17. The X-ray imaging system of claim 16, wherein the controller allocates a predetermined marker to the registered detector to represent activation or non-activation thereof, and
wherein the communicator transmits the first control information including the allocated predetermined marker to the detector.

18. The X-ray imaging system of claim 16, wherein
the detector profile information further comprises at least one from among a type and a serial number of the detector, and
the memory stores the detector profile information to an available detector list of the X-ray imaging system.

19. The X-ray imaging system of claim 18, wherein
the controller sets operation conditions for performing imaging using the detector based on the detector correction information, and
the detector correction information comprises at least one from among detector step difference correction information indicating an amount of step difference correction of the detector for performing imaging and defective pixel compensation information indicating a range of defective pixel compensation of the detector for performing imaging.

20. The X-ray imaging system of claim 17, wherein the allocated predetermined marker comprises at least one from among a character, a number, a symbol, a color, and an image.

21. The X-ray imaging system of claim 16, wherein
the controller is further configured to determine whether the detector profile information is broadcast on a wired network or a wireless network to which the X-ray imaging system is connected, access an unregistered detector corresponding to the detector profile information being broadcast on the wired network or the wireless network,
the communicator receives the broadcast detector profile information from the unregistered detector;
the memory stores the detector profile information in a candidate detector list, and
the detector profile information comprises at least one from among a type and a serial number of the unregistered detector.

22. The X-ray imaging system of claim 21, wherein the memory stores the detector profile information on the candidate detector list to an available detector list of the X-ray imaging system.

23. The X-ray imaging system of claim 22, wherein
the communicator receives the detector correction information from the detector having the detector profile information stored in the available detector list,
the controller sets operation conditions for performing imaging using the detector based on the detector correction information received from the detector, and
the detector correction information comprises at least one from among detector step difference correction information indicating an amount of step difference correction of the detector for performing imaging and defective pixel compensation information indicating a range of defective pixel compensation of the detector for performing imaging.

24. A detector for transmitting detector correction information to an X-ray imaging system, the detector comprising:
a communicator configured to receive, from the X-ray imaging system, a request to access the detector via a virtual IP address of the detector, and transmit detector profile information of the detector to the X-ray imaging system in response to the request, the detector profile information comprising a real IP address of the detector and receive, from the X-ray imaging system, first control information; and
a controller configured to deactivate the virtual IP address of the detector and activate the real IP address of the detector based on the first control information;
wherein the communicator is further configured to transmit the detector correction information to the X-ray imaging system.

25. The detector of claim 24, wherein the detector profile information comprises at least one from among a type, and a serial number of the detector, and
wherein the detector correction information comprises at least one from among detector step difference correction information indicating an amount of step difference correction of the detector for performing imaging and defective pixel compensation information indicating a range of defective pixel compensation of the detector for performing imaging.

26. The detector of claim 24, wherein
the first control information includes an allocated predetermined marker to the detector, and
wherein the allocated predetermined marker comprises at least one from among a character, a number, a symbol, a color, and an image, and the detector further comprises a display configured to display a change of a state of the detector by using the allocated predetermined marker.

27. The detector of claim 26, wherein
the communicator receives second control information from the X-ray imaging system,
the controller deactivates the real IP address of the detector and activates the virtual IP address of the detector based on the second control information, and
the display displays the change of the state of the detector by changing the allocated predetermined marker.

28. A detector for transmitting detector correction information to an X-ray imaging system, the detector comprising:
a communicator configured to broadcast detector profile information to a network to which the X-ray imaging system is connected;
receive, from the X-ray imaging system, first control information; and
a controller configured to stop the broadcasting based on the first control information,
wherein the communicator further configured to transmit the detector correction information to the X-ray imaging system.

29. The detector of claim 28, wherein the first control information includes an allocated predetermined marker, and
wherein the detector further comprises a display configured to display a change of a state of the detector by using the allocated predetermined marker.

30. The detector of claim 29, wherein
the communicator receives second control information from the X-ray imaging system, and starts broadcasting of the detector profile information to the network based on the second control information, and
the display displays the change of the state of the detector by changing the allocated predetermined marker when the broadcasting by the detector is started.

31. A non-transitory computer-readable recording medium having recorded thereon a program for executing the method of claim 1.

32. A detector for transmitting information for setting operation conditions of the detector in an X-ray imaging system, the detector comprising:
at least one processor operable to read and operate according to instructions within a computer program; and
at least one memory operable to store at least portions of said computer program for access by the at least one processor,
wherein said computer program includes algorithms to cause the at least one processor to implement:
receiving, from the X-ray imaging system, a request to access the detector via a virtual IP address of the detector;
transmitting detector profile information of the detector to the X-ray imaging system in response to the request, the detector profile information comprising a real IP address of the detector;
receiving, from the X-ray imaging system, first control information;
deactivating the virtual IP address of the detector and activating the real IP address of the detector based on the first control information; and
transmitting the detector correction information to the X-ray imaging system.

* * * * *